United States Patent [19]
Snell et al.

[11] Patent Number: 5,487,754
[45] Date of Patent: Jan. 30, 1996

[54] METHOD AND APPARATUS FOR REPORTING AND DISPLAYING A SEQUENTIAL SERIES OF PACING EVENTS

[75] Inventors: Jeffery D. Snell, Northridge; Harold C. Schloss, Los Angeles; Brian M. Mann, Beverly Hills; John W. Poore, South Pasadena; Roy B. Medlin, West Hills, all of Calif.

[73] Assignee: Pacesetter, Inc., Sylmar, Calif.

[21] Appl. No.: 328,217

[22] Filed: Oct. 25, 1994

Related U.S. Application Data

[62] Division of Ser. No. 846,460, Mar. 2, 1992, Pat. No. 5,431,691.

[51] Int. Cl.$^6$ ..................................................... A61N 1/37
[52] U.S. Cl. ............................................................ 607/27
[58] Field of Search ................................. 607/27; 128/697

[56] References Cited

U.S. PATENT DOCUMENTS

| | | | |
|---|---|---|---|
| 4,320,767 | 3/1982 | Villa-Real | 128/680 |
| 4,333,475 | 6/1982 | Moreno et al. | 128/711 |
| 4,399,821 | 8/1983 | Bowers | 128/630 |
| 4,513,743 | 4/1985 | van Arragon et al. | 128/419 PG |
| 4,559,947 | 12/1985 | Renger et al. | 128/419 PG |
| 4,596,255 | 6/1986 | Snell et al. | 128/419 PT |
| 4,791,936 | 12/1988 | Snell et al. | 128/697 |
| 4,809,697 | 3/1989 | Causey, III et al. | 128/419 PT |
| 4,940,052 | 7/1990 | Mann et al. | 128/419 PG |
| 4,944,299 | 7/1990 | Silivan | 128/419 PG |
| 5,016,634 | 5/1991 | Vock et al. | 128/419 PT |
| 5,040,534 | 8/1991 | Mann et al. | 128/419 PG |

OTHER PUBLICATIONS

Sanders et al., "Data Storage and Retrieval by Implantable Pacemakers for Diagnostic Purposes," *Pace,* vol. 7, pp. 1228–1233 (Nov.–Dec. 1984, Part II).

Levine, P. A., "Diagnostic Data: An Aid to the Follow–up and Assessment of the Pacing System," *Journal of Electro-physiology,* vol. 1, pp. 396–403 (1987).

"Chorus 6003–6033 Implantable Dual–Chamber Pulse Generator DDD MO," *Physician's Manual,* pp. 40–41 (ELA Medical, Minnetonka, MN–1990 or earlier).

Luceri et al., "Improved Patient Surveillance and Data Acquisition with a Third Generation Implantable Cardioverter–Defibrillator," *Pace,* vol. 14, pp. 1870–1874 (Nov. 1991. Part II).

*Primary Examiner*—William E. Kamm
*Attorney, Agent, or Firm*—Harold C. Schloss

[57] ABSTRACT

An implantable pacemaker continuously records pacing events and their respective rates of occurrence in sequence, as they occur, into an Event Record stored in a circular buffer. The circular buffer always contains the most recent events and rates collected. The recording of the pacing events selectively occurs at every event, or at sampling rates of one event per fixed sample interval. A programming device, coupled to the implantable pacemaker through a telemetry link, selectively retrieves the recorded pacing events and rates from the Event Record and reports subsets thereof in condensed or summarized form using numerical and/or graphical formats. The pacing event data collected in the Event Record is three-dimensional in that each pacing event includes a pacemaker event, an associated pacemaker or heart rate, and a real time interval. The programming device also calculates and reports statistical information from the data collected in the Event Record. The Event Record provides a base recording that establishes the behavior of the pacemaker in a particular patient under ascertainable conditions.

35 Claims, 14 Drawing Sheets

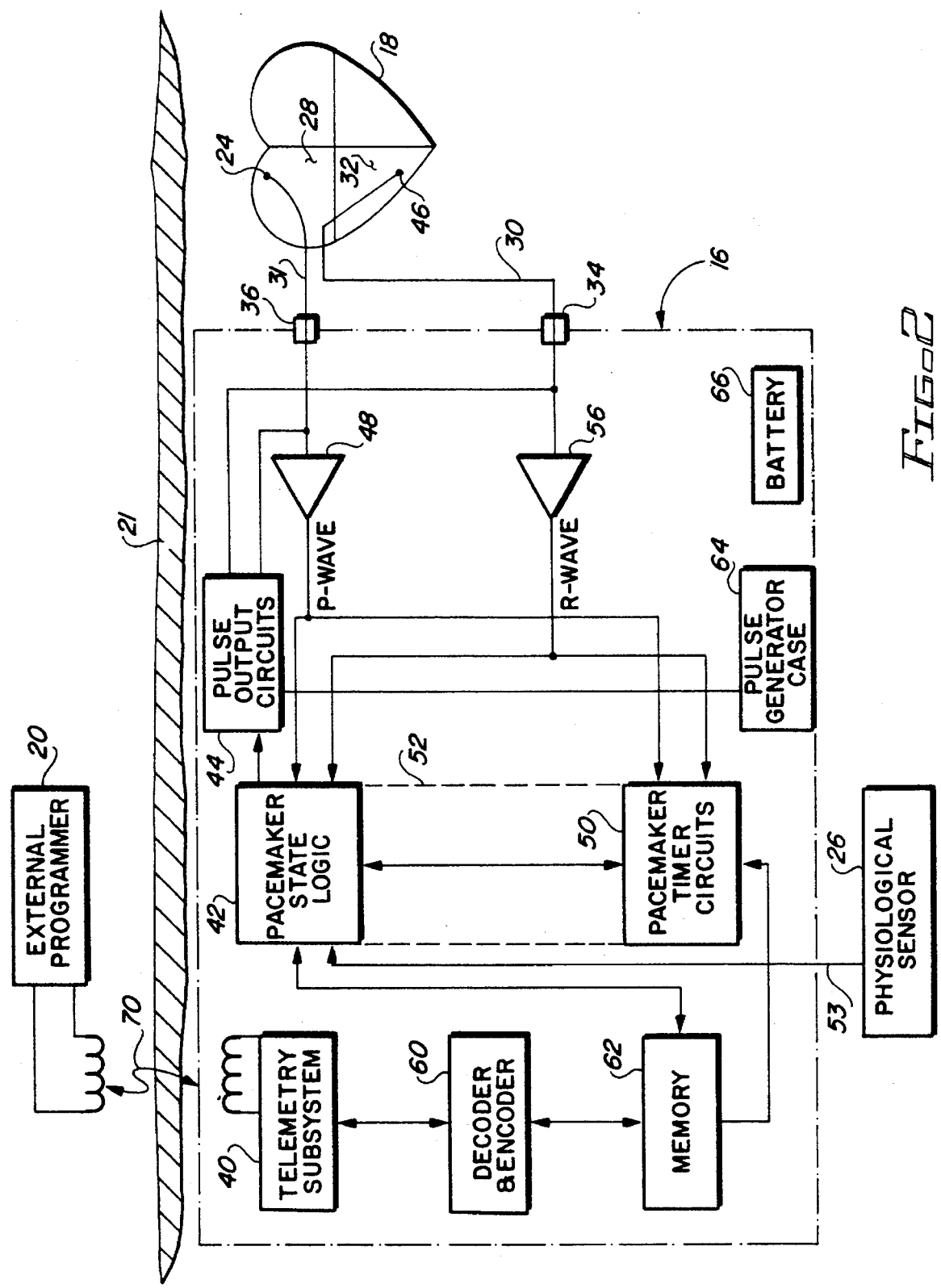

Pacesetter Systems, Inc.
A Siemens Company ©1991

Synchrony® II

APS: Version: Proto 3038 - 1234

Apr 1 1983 1:00 am
MODEL: 2022  SERIAL: 14209

PATIENT: _____

PHYSICIAN: _____

2:1 Block Rate at 165 ppm

EVENT RECORD

Mode _____ DDDR
Sensor _____ ON
Rate _____ 70 ppm
Max Track _____ 110 ppm
Maximum Sensor Rate _____ 110 ppm
A-V Delay _____ 175 msec
Rate Resp. A-V Delay ____ ENABLE Note: The above values were obtained
when the event record was interrogated.

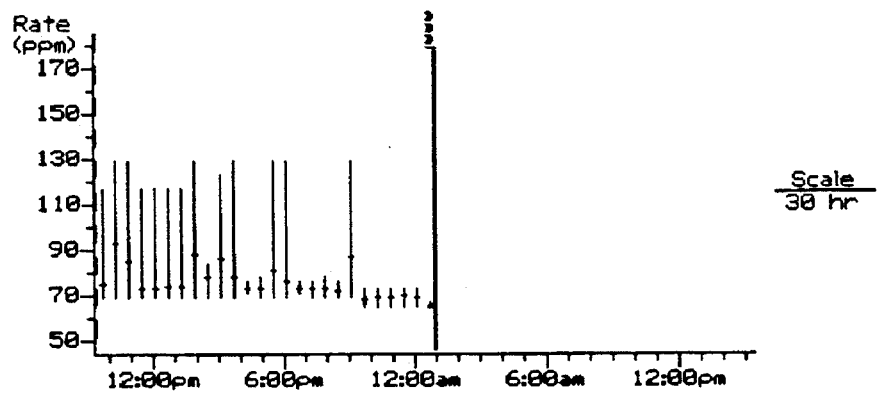

KEY:
■=AV ▣=PV ✶=PVE
A=AR P=PR O=OFF
■=Paced s=Sensed

*Fig. 11*

Pacesetter Systems, Inc.
A Siemens Company ©1991
APS: Version: Proto 3038 - 1234

Synchrony® II

Apr 1 1983 1:00 am
MODEL: 2022    SERIAL: 14209

PATIENT: _____

PHYSICIAN: _____

2:1 Block Rate at 165 ppm ( EVENT BAR GRAPH )

Mode _____ DDDR
Sensor _____ ON
Rate _____ 70 ppm
Max Track _____ 110 ppm
Maximum Sensor Rate _____ 110 ppm
A-V Delay _____ 175 msec
Rate Resp. A-V Delay _____ ENABLE Note: The above values were obtained
when the event record was interrogated.

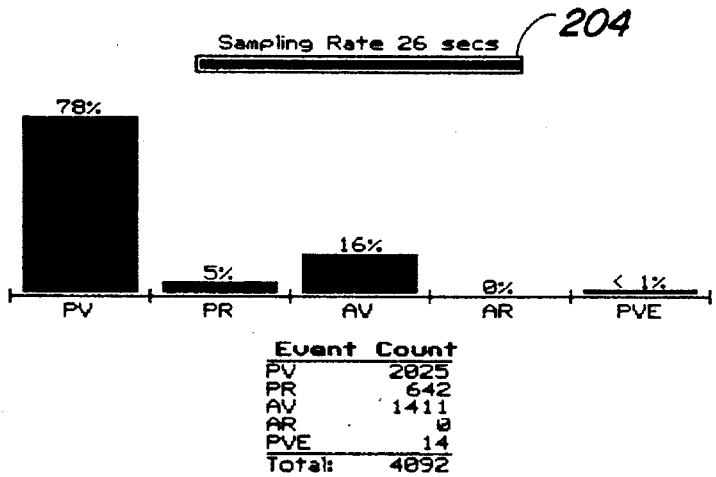

| Event Count | |
|---|---|
| PV | 2025 |
| PR | 642 |
| AV | 1411 |
| AR | 0 |
| PVE | 14 |
| Total: | 4092 |

Total Time _____ 0d 15h 21m 24s
Starting Time _____ 9:38:36am
Ending Time _____ 1:00:00am Percent Paced in Atrium _____ 34%
Percent Paced in Ventricle _____ 84%

Total Time at Max Track Rate _____ 0d 0h 0m 0s
Duration of Longest Episode at MTR _____ 0d 0h 0m 0s
Number of Episodes at MTR _____ 0

Total Time at Sensor Rate > 109 ppm _____ 0d 0h 58m 58s
Duration of Longest Episode at MSR _____ 0d 0h 8m 40s
Number of Episodes at MSR _____ 7

*FIG. 17*

 Synchrony®II
Pacesetter® Systems, Inc.
A Siemens Company ©1991
APS: Version: Proto 3038 - 1234
Apr 1 1983 1:00 am
MODEL: 2022    SERIAL: 14209
PATIENT: _____
PHYSICIAN: _____
2:1 Block Rate at 165 ppm
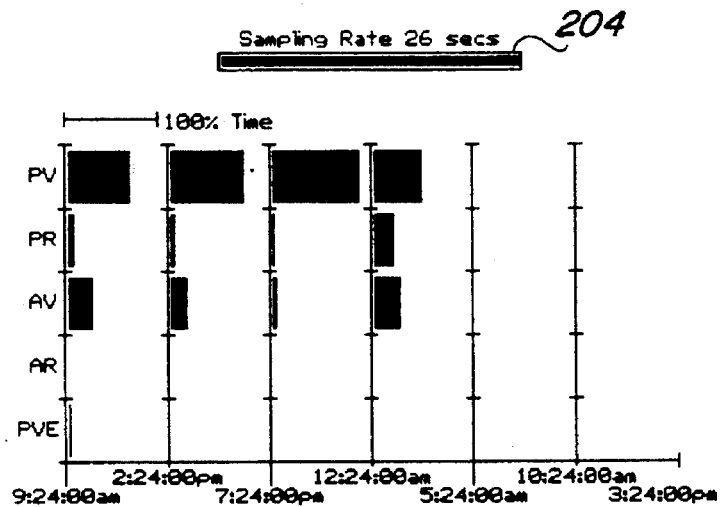
| EVENT TIME GRAPH |
| Mode | DDDR |
| Sensor | ON |
| Rate | 70 ppm |
| Max Track | 110 ppm |
| Maximum Sensor Rate | 110 ppm |
| A-V Delay | 175 msec |
| Rate Resp. A-V Delay | ENABLE |
Note: The above values were obtained when the event record was interrogated.
| Event | Count |
|-------|-------|
| PV | 2025 |
| PR | 642 |
| AV | 1411 |
| AR | 0 |
| PVE | 14 |
| Total | 4092 |
*Fig. 18*

 Synchrony® II

Pacesetter® Systems, Inc.
A Siemens Company ©1991
APS: Version: Proto 3038 - 1234

Apr 1 1983 1:00 am
MODEL: 2022    SERIAL: 14289

PATIENT: _____

PHYSICIAN: _____

2:1 Block Rate at 165 ppm ( RATE BAR GRAPH )

Mode .................................... DDDR
Sensor .................................. ON
Rate .................................... 70 ppm
Max Track ............................... 110 ppm
Maximum Sensor Rate ..................... 110 ppm
A-V Delay ............................... 175 msec
Rate Resp. A-V Delay .................... ENABLE Note: The above values were obtained
when the event record was interrogated.

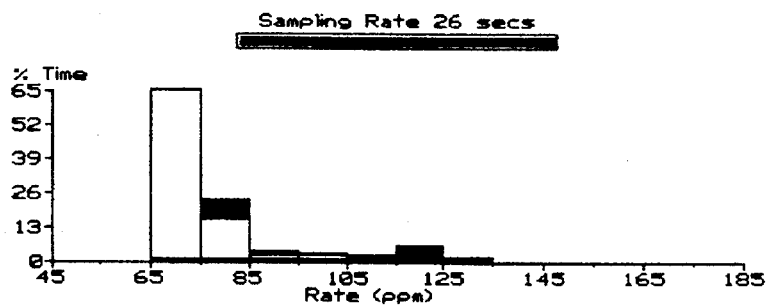

Total Time ............................................. 0d 15h 21m 24s
Starting Time .......................................... 9:38:36am
Ending Time ............................................ 1:00:00am Percent Paced in Atrium ................................ 34%
Percent Paced in Ventricle ............................. 84%

Total Time at Max Track Rate ........................... 0d 0h 0m 0s
Duration of Longest Episode at MTR ..................... 0d 0h 0m 0s
Number of Episodes at MTR .............................. 0

Total Time at Sensor Rate > 109 ppm .................... 0d 0h 58m 58s
Duration of Longest Episode at MSR ..................... 0d 0h 8m 40s
Number of Episodes at MSR .............................. 7

FIG. 19

Pacesetter® Systems, Inc.
A Siemens Company ©1991
APS: Version: Proto 3038 - 1234
Synchrony®II
Apr 1 1983 1:00 am
MODEL: 2022    SERIAL: 14209
PATIENT: _____
PHYSICIAN: _____
2:1 Block Rate at 165 ppm
( RATE TIME GRAPH )
Mode _____ DDDR
Sensor _____ ON
Rate _____ 70 ppm
Max Track _____ 110 ppm
Maximum Sensor Rate _____ 110 ppm
A-V Delay _____ 175 msec
Rate Resp. A-V Delay _____ ENABLE
Note: The above values were obtained
when the event record was interrogated.
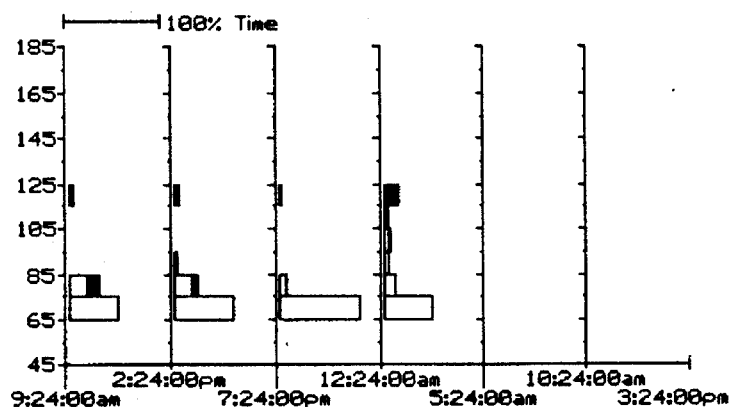
FIG-20

METHOD AND APPARATUS FOR REPORTING AND DISPLAYING A SEQUENTIAL SERIES OF PACING EVENTS

This is a divisional of patent application Ser. No. 07/846,460, filed on Mar. 2, 1992, now U.S. Pat. No. 5,431,691, granted Jul. 11, 1995.

BACKGROUND OF THE INVENTION

FIELD OF THE INVENTION

The present invention relates to implantable medical devices and methods, and more particularly to an implantable pacemaker that records the occurrence and rate of specified pacemaker events in sequence as such events occur, either on an every event or a sampled basis. Such sequence of events and their respective rates, when retrieved from the pacemaker, is useful as a diagnostic tool for analyzing the performance of the pacemaker and for aiding in optimally programming the pacemaker for a particular patient.

A pacemaker is an implantable medical device that delivers electrical stimulation pulses to a patient's heart, as required, in order to keep the heart beating at a desired rate. Early pacemakers provided stimulation pulses at a fixed rate or frequency, such as 70 pulses per minute (ppm), thereby maintaining the heart beat at that fixed rate. Subsequently, pacemakers were designed to not only stimulate the heart, but also to monitor the heart. If a natural heart beat was detected within a prescribed time period (usually referred to as the "escape interval"), no stimulation pulse was delivered, thereby allowing the heart to beat on its own without consuming the limited power of the pacemaker. Such pacemakers are referred to as "demand pacemakers" because stimulation pulses are provided only as demanded by the heart.

Early demand pacemakers had a fixed base rate associated therewith. In later versions, the base rate was programmably selectable, and thereafter became commonly known as the "programmed rate." If the heart was able to beat on its own at a rate exceeding the base (or programmed) rate, then no stimulation pulses were provided. However, if the heart was not able to beat on its own at a rate exceeding the base rate, then stimulation pulses were provided to ensure that the heart would always beat at least at the base (or programmed) rate.

In recent years, rate-responsive pacemakers have been developed that automatically change the rate at which the pacemaker provides stimulation pulses as a function of a sensed parameter (physiological or other). The sensed parameter provides some indication of whether the heart should beat faster or slower, depending upon the needs of the pacemaker user. Thus, for example, if a patient is at rest, there is generally no need for a faster-than-normal heart rate, so the rate-responsive pacemaker maintains the pacing rate at a normal value, such as 60 ppm. However, if the patent is exercising, or otherwise physiologically active, there is a need for the heart to beat much faster, such as 100 beats per minute. For some patients, the heart is not able to beat faster on its own, so the pacemaker must assist. In order to do this effectively, the physiological need for the heart to beat faster must first be sensed, and the pacing rate of the rate-responsive pacer must be adjusted accordingly. Hence, rate-responsive pacemakers are known in the art as devices that increase and decrease the "base rate" as a function of sensed need (physiological or other).

For purposes of the present application, the following definitions are provided, which are intended as generic definitions that may be used for either single- or dual-chamber pacing. Single-chamber pacing relates to monitoring and/or pacing within only one chamber of the heart, the atrium or the ventricle. Dual-chamber pacing relates to monitoring and/or pacing in both chambers of the heart. A "P-wave" is an electrical signal manifest when the atrium contracts naturally. An "R-wave" is an electrical signal manifest when the ventricle contracts naturally. An "A-pulse" is an electrical stimulation pulse that is generated by the pacemaker and delivered to the atrium in order to force an atrial contraction. A "V-pulse" is an electrical stimulation pulse that is generated by the pacemaker and delivered to the ventricle in order to force a ventricular contraction. A "cardiac cycle" is the time it takes the heart to cycle through one complete sequence of atrial and ventricular contractions. A "pacing cycle" is a cardiac cycle as measured or determined within the pacemaker. The cardiac or pacing cycle may be measured between any two recurring points or events associated with such sequence of contractions, such as P-waves, R-waves, A-pulses, V-pulses, or combinations thereof. The cardiac cycle may be represented by an A-pulse followed by a V-pulse extending to the next A-pulse or P-wave, by an A-pulse followed by an R-wave extending to the next A-pulse or P-wave, by a P-wave followed by a V-pulse extending to the next A-pulse or P-wave, or by a P-wave followed by an R-wave extending to the next A-pulse or P-wave.

Continuing with the definition of terms, a "PVE" is a premature ventricular event, i.e., an R-wave that occurs without a sensed intervening P-wave or A-pulse. The "MTR" is the maximum tracking rate of the pacemaker, and defines a minimum time interval that must elapse after a specified ventricular event, e.g., an R-wave or a V-pulse, before another paced ventricular event (V-pulse) is allowed to take place in response to a sensed P-wave. The "MSR" is the maximum sensor rate, and is used in conjunction with rate-responsive pacemakers to define the maximum pacing rate that the pacemaker may assume under sensor drive. Both the MTR and the MSR are parameters used to limit the maximum rate at which a pacemaker is allowed to provide stimulation pulses on demand. These need not be the same rate.

In addition to the above terms, it should also be noted that modern programmable pacemakers may be programmed to operate in several different modes. By convention, operating modes are designated with a three or four letter code. The first letter of the code signifies the chambers of the heart where pacing may occur, with "A" signifying the atrium; "V" the ventricle; "O" none; and "D" both the atrium and ventricle or dual chamber. The second letter of the code signifies the chambers of the heart where sensing may occur, using the same letters. The third letter of the code signifies the type of action taken by the pacemaker in response to a native complex (P- or R-wave), with "O" being asynchronous pacing-namely, no sensing; "I" indicating that the stimulation pulse is inhibited if sensing occurs; "T" indicating that a stimulation pulse is delivered or triggered in response to a sensed P- or R-wave (useful for diagnostic purposes); and "D" indicating both inhibiting or triggering functions. In a DDD pacemaker, a sensed P-wave inhibits the atrial output pulse but triggers a ventricular output after a preset delay (the AV interval). If an R-wave is sensed before release of the atrial pulse, it inhibits and resets both the atrial and ventricular pulses. If an R-wave is sensed within the alert period of the AV delay, it inhibits the ventricular stimulus and resets the pacemaker. If an R-wave is sensed during a special detection window occurring shortly after an atrial stimulus, it triggers a ventricular output pulse. A fourth letter signifies the extent of programmability, communicating or telemetric features, and rate-responsive features of the pacemaker, if any. An "R" is used as the fourth letter to indicate a rate-responsive pacemaker with the sensor programmed ON (meaning that the sensor is enabled to detect physiological or other activity and is connected to the pacemaker circuits so as to adjust the pacemaker's pacing rate as a function of such sensed physiological or other activity). An "O" in the fourth position means that the pacemaker is not capable of being adjusted (programmed) noninvasively and does not have rate-modulated capability. A "P" means that one or two parameters can be programmed or adjusted noninvasively. An "M" in the fourth position means that the pacemaker has three or more parameters which can be programmed. "C" means the device has "M" programming capability and can communicate with the programmer. Again "R" means rate-modulated capability; it also reflects "C" capability as well.

Nearly all implantable pacemakers in use today, as well as similar implantable medical devices, can be configured by the attending physician in the physician's office. The process of configuring a pacemaker is commonly referred to as "programming." The programming process uses noninvasive telemetry to customize the operation of the pacemaker to fit the individual needs of the patient. Customization is achieved by adjusting a set of "pacemaker parameters" to values that cause the pacemaker to work in an optimum way for the particular patient within whom the device has been implanted.

Disadvantageously, as the complexity of new implantable devices has evolved over the past several years, it has become increasingly difficult for the attending physician, or other medical personnel, to determine how the pacemaker should be programmed in order to provide the most effective therapy for a given patient. This difficulty is particularly manifest with recent-generation pacemakers that tend to be more automatic and autonomous than earlier-generation pacemakers, which recent-generation pacemakers may be controlled by input signals received from a multiplicity of internal sensors. For example, recent "rate-responsive" pacemakers, as indicated above, provide stimulation pulses to a patient's heart, as needed, based on the input signals received from one or more physiological or other sensors that attempt to predict just how fast the patient's heart should beat in order to meet the patient's physiological needs.

A significant factor that makes the optimum programming of recent-generation pacemakers more difficult is the variation in each of the sensor inputs from patient to patient. Such variation is caused by numerous factors, including the patient's physical structure, the implant site, the particular disease or malady the patient has and its progression within the patient's heart or other body tissue, the drugs being taken by the patient to treat his or her condition, etc. Thus, to appropriately program the pacemaker for a given patient, the physician must anticipate how the pacemaker will operate given all of these variables, and given all the environments and activities that the patient is expected to encounter. Programming a modern pacemaker may thus comprise an extremely formidable task, for which task there is a critical need for programming aids to assist the physician in anticipating the pacemaker response for each particular patient.

It is known in the art to use programming aids and devices with implantable pacemakers to facilitate the physician's understanding of the pacemaker's programmed operation as it interacts with the patient's natural cardiac activity. For many years, the primary programming aid and source of diagnostic data for use in analyzing the operation of an implanted pacemaker has been the surface electrocardiogram (ECG), in which both pacemaker and heart activity are recorded and displayed simultaneously. From the ECG, the activity of the heart—including the contraction of the atria, the contraction of the ventricles, and the timing therebetween—could be displayed. From the pacemaker, the activity of the pacemaker—including when a heart contraction was sensed and when a stimulation pulse was generated—could likewise be monitored through the use of marker signals telemetered from the pacemaker to a remote (nonimplanted) receiver, where such signals were processed and displayed as marks superimposed on the ECG waveform.

In recent years, specific programming devices have been developed that not only allow the pacemaker parameters to be noninvasively set to desired values, but that also allow the operation of the pacemaker and the heart to be monitored without having to obtain a surface ECG. Such is accomplished by transmitting an intercardiac ECG signal, either alone or in combination with marker signals. See, e.g., U.S. Pat. Nos. 4,559,947; 4,596,255; 4,791,936; and 4,809,697.

Disadvantageously, while such prior art programming devices have done much to facilitate communications with and analysis of implantable programmable pacemakers, they all suffer from one major drawback—they are limited to real-time data analysis. This is true even though some provide the capability of capturing a short segment, e.g., 30 seconds, of the intracardiac ECG signal, which intracardiac ECG signal, once captured, can advantageously be expanded, compressed, or otherwise processed in a desired manner in order to better examine it. Unfortunately, in order to properly assess some types of problems that may develop for a given patient having an implanted pacemaker, it is frequently necessary to examine the intracardiac signal, or at least the main components thereof, over a much longer period of time, e.g., minutes, hours, days, weeks, or months. What is needed, therefore, is not only a programming device that facilitates the physician's ability to understand the interaction of the implanted device with the patient and to evaluate active clinical problems, but a device that provides the physician with sufficient data to allow the performance of the system to be assessed over an extended period of time.

Moreover, in some instances, it may be necessary, or at least desirable if a proper analysis of a particular problem is to be made, to carefully examine selected cardiac signals at a particular moment in time, which particular moment in time may have occurred at a time prior to the evaluation. Such analysis could reveal, for example, whether a PVC occurred, or if a particular cardiac cycle was made up of paced events or sensed events, or both. Unfortunately, there are no known devices that conveniently provide such past information with sufficient detail to enable such a careful analysis to be made. Hence, there is also a need for a device that allows the past interaction between a pacemaker and a patient's heart to be carefully examined and studied.

The commonly used solution to the above-described problem is to use a Holter Monitor, or equivalent external device. A Holter Monitor is essentially a recorder that is carried by the patient. The Holter Monitor senses the surface ECG signal and records it. Thus, after the data-collection period during which the Holter Monitor is used (usually 24 hours), the number of specific cardiac events that occurred, e.g., the number of ventricular contractions, may be determined.

Disadvantageously, Holter Monitors, and equivalent devices, are external devices that must be carried by the patient continuously throughout the monitoring period. Such carrying can be a nuisance and a bother to the patient. Further, such externally-carried recording devices suffer from numerous limitations. One of the main limitations is their inability to consistently identify the high-frequency pacing stimulus generated by the pacemaker. This is particularly the case when the pacemaker generates a bipolar pacing pulse, which pacing pulse is of relatively low amplitude and difficult to detect (compared to a unipolar pacing pulse). Thus, although the contraction of the heart may be recordable, there is no way of easily determining whether the contraction was a natural contraction or a paced contraction. Further, if a pacing pulse is generated and the heart does not respond to it (i.e., if there is a lack of "capture"), such lack-of-capture event may not be detectable.

Another limitation of Holter Monitors, and equivalent externally-carried recording devices, is that they have no way of monitoring, and hence recording, the internal state of the implanted pacemaker. A knowledge of the internal state of a pacemaker would be invaluable in determining the actual pacemaker behavior. Advantageously, the implanted pacemaker "knows" exactly when it paces and senses on each channel and how it is responding to every input signal. Thus, what is needed is an implanted pacemaker that is equipped to track and report its behavior over time; and, upon command, provide such information to an attending physician.

There are at least two prior art devices known to the inventors that attempt to address at least some of the above needs. On such device is the Cosmos™ 283-01 pacemaker marketed by Intermedics, Inc. of Angleton, Tex. The Cosmos 283-01, using a feature termed "Diagnostic Data™," counts the number of specific cardiac events that occur during the monitoring period. See, Sanders et al., "Data Storage and Retrieval by Implantable Pacemakers for Diagnostic Purposes," PACE, Vol. 7, pp. 1228–33 (1984); and Levine, P.A., "Diagnostic Data: An Aid to the Follow-Up and Assessment of the Pacing System," *Journal of Electrophysiology*, Vol. 1, pp. 144–53 (1987). The other device is the CHORUS™ 6033 pacemaker marketed by ELA Medical, of Montrouge, France. Both of these devices, and similar devices described in the literature, see, e.g., U.S. Pat. No. 4,513,743 (van Arragon et al.), are thus able to determine the total number of occurrences of a selected cardiac event, e.g., the number of times that an atrial pulse is issued; or the number of times that an atrial-to-ventricular (AV) interval has a delay that falls within defined time limits. Knowing the total number of occurrences of such events is a helpful diagnostic tool in assessing some pacemaker/patient problems. Disadvantageously, however, such devices do not record the frequency ranges (rate) of the cardiac events that are counted. Nor do they record the sequence in which the cardiac events occur, or the time at which the cardiac events occurred. Such limitations prevent numerous evaluations from being performed, such as the composition (sensed or paced events) of a prior sequence of cardiac cycles under stressed conditions, the variations in the heart rate over a past period of time, the determination of sensor responsiveness, or an assessment of chronotropic competence. What is needed, therefore, is an implantable medical device that not only detects and records the occurrence of specified cardiac events, and in particular pacemaker events or states, but that also determines and records the sequence of such events and the rate of occurrence of such events.

The present invention advantageously addresses the above and other needs.

SUMMARY OF THE INVENTION

The present invention provides a method and system for retrieving and reporting information stored by pacemakers that record pacing data in an Event Record. The data recorded in such Event Record comprise a plurality of specified pacing events associated with the operation of an implanted medical device, e.g., either a dual- or single-chamber pacemaker. Such pacing events are recorded in sequence, as they occur, into a circular buffer so that the buffer always contains the most recent data collected. The pacing events recorded in the Event Record include discrete events that occur in the implanted device and the associated pacing or heart rate. The recording of the pacing events may selectively occur at every event, for highest resolution, or at sampling rates of one event per fixed sample interval.

In accordance with one aspect of the invention, an external programming device is selectively coupled to an implantable pacemaker through a telemetry link. The programming device includes processing means for retrieving the recorded pacing event data from the Event Record stored in the pacemaker. The processing means allows subsets of the Event Record data to be selectively reported in both numerical and graphical formats. Advantageously, such numerical and graphical formats may selectively include condensed and/or summarized versions of the data.

In accordance with a further aspect of the invention, the programming device retrieves the data from the implantable pacemaker, or other implantable device, at a known time. Using this time as a reference, the programming device is able to assign a time of occurrence to all the data sequentially collected in the Event Record of the pacemaker. Thus, when the data of the Event Record is processed and displayed, it may be displayed not only as a function of the type and rate of the event that occurred, as well as in the sequence in which a plurality of the events occurred, but also as a function of time of occurrence.

Thus, in accordance with another aspect of the invention, the data collected in the Event Record is essentially three-dimensional—each pacing event comprising a pacemaker event, an associated pacemaker or heart rate, and a real time interval (represented by the rate data, if sampling every event; or by the sampling interval, if sampling at a fixed rate). Such three-dimensional data is summarized by projecting or printing all or selected portions of the data onto a two dimensional plane with a horizontal and vertical axis. The data may be selectively displayed or printed on such plane with: (1) time of occurrence on the horizontal axis and event type or rate on the vertical axis; (2) rate on the horizontal axis and cumulative time on the vertical axis; or (3) events on the horizontal axis and cumulative time on the vertical axis. In some displays, a third dimension may be added to the two dimensional display by including, e.g., event type icons or other annotations to the display, or selected stacked bar graphs.

In accordance with yet another aspect of the invention, insightful statistical information may be calculated from the data collected in the Event Record. Such statistical information may include, for example, the percent of paced pulses in the atrium and/or ventricle; the total time of operation at a maximum tracking rate (MTR), the duration of the longest and/or shortest MTR episodes; the number of episodes at the MTR; the total time at the maximum sensor rate (if a sensor is used); the duration of the longest and/or shortest maximum sensor rate episodes; the number of episodes at the maximum sensor rate, and the like.

The invention may also be characterized as a method for reporting a sequential series of pacing events as recorded in sequence in an event record by a pacemaker. Such method includes at least the steps of: (a) retrieving the event record from the pacemaker; (b) processing the event record to determine the time each pacing event occurred, and to maintain the order of occurrence and associated rate; and (c) displaying the pacing events as a function of type, rate, and time of occurrence.

BRIEF DESCRIPTION OF THE DRAWINGS

The above and other aspects, features and advantages of the present invention will be more apparent from the following more particular description thereof, presented in conjunction with the following drawings wherein:

FIG. 2 is a block diagram of the pacemaker of FIG. 1 and illustrates how an external programmer is used therewith;

FIG. 11 illustrates a typical Event Record report as printed by the APS-II/MTM programmer;

FIG. 17 is a typical Event Record report of the Event Bar Graph as printed by the APS-II/MTM programmer based on data collected using a sampling time of 26 seconds (corresponding to a data collection period of around 30 hours);

FIG. 18 is a typical Event Record report of the Event Time Graph as printed by the APS-II/MTM programmer based on data collected using a sampling time of 26 seconds;

FIG. 19 is a typical Event Record report of the Rate Bar Graph as printed by the APS-II/MTM programmer based on data collected using a sampling time of 26 seconds; and FIG. 20 is a typical Event Record report of the Rate Time Graph as printed by the APS-II/MTM programmer based on data collected using a sampling time of 26 seconds.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Before describing the reporting and displaying features associated with the present invention, it will be helpful to review the main components of a pacing system, i.e., the pacemaker and the programmer, and to provide an overview of their operation.

The Pacemaker

Figure 1:
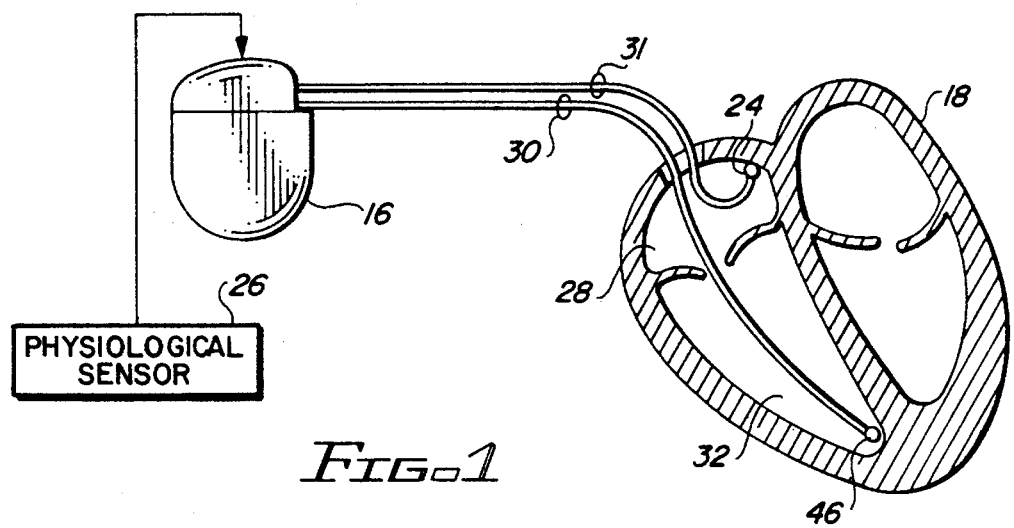
FIG. 1 shows an implantable pacemaker having a physiological sensor coupled to a heart.

The pacemaker side of a pacing system is shown in FIG. 1. As seen in FIG. 1, an implantable pacemaker 16 has a physiological sensor 26. Although a sensor 26 is shown coupled to the pacemaker 16, it is to be understood that the present invention may be used with pacemakers that do not have a sensor 26 coupled thereto, or to pacemakers wherein such a sensor has been programmed to an OFF or PASSIVE mode. The pacemaker 16 is coupled to a heart 18 by way of pacing leads 30 and 31. The pacing lead 30 has an electrode 46 positioned in the right ventricle 32 of the heart 18. The lead 30 is thus typically referred to as the ventricular lead, and the signals generated by the pacemaker for delivery to the heart through electrode 46 over lead 30, or the signals sensed through electrode 46 and the lead 30, are processed by circuits in what is known as the ventricular channel of the pacemaker 16. Similarly, the pacing lead 31 has an electrode 24 positioned in the right atrium 28 of the heart 18. The lead 31 is thus typically referred to as the atrial lead, and the signals generated by the pacemaker for delivery to the heart through the electrode 24 over lead 31, or the signals sensed through electrode 24 and the lead 31, are processed by circuits in what is known as the atrial channel of the pacemaker 16.

Note that what is shown in FIG. 1 is a dual-chamber pacemaker, in that sensing and/or pacing may occur in both chambers of the heart 18, i.e., in the atrium 28 and/or the ventricle 32. It is to be understood that the present invention may be used with either dual-chamber pacing, as shown in FIG. 1, or with single-chamber pacing, where sensing and pacing occur in only one chamber of the heart. It should also be understood that most pacemakers that provide a dual-chamber configuration, such as is illustrated in FIG. 1, may also be programmed to operate in a single-chamber mode.

Referring next to FIG. 2, a more detailed block diagram of the dual-chamber pacemaker 16 is shown. Note that as shown in FIGS. 1 and 2, the atrial lead 31 and the ventricular lead 30 are unipolar leads. In unipolar operation, the tip electrode 24 or 46 provides one signal path, with the return signal path being provided through conductive body tissue and fluids to an exposed portion of the pacemaker case 64. It is to be understood, however, that either one or both of the leads 30 or 31 could be bipolar leads, having two electrodes, in which case the signal return path is provided through the other electrode (which other electrode is typically a ring electrode that is positioned only a few centimeters from the tip electrode).

As suggested in FIG. 2, the pacemaker 16 is in telecommunicative contact with an external programmer 20 via a telemetry link 70. The programmer 20 includes a telemetry receiver and monitor external to the patient's skin 21. The pacemaker 16 includes a telemetry subsystem 40 for transmitting data and parameter values to the external telemetry transmitter and receiver of the external programmer 20, and for receiving data instructions and the like from the external programmer 20. Data instructions received from the external programmer 20 are decoded in decoder and encoder 60 and stored in memory 62. Likewise, data and parameter values to be sent to the external programmer 20 are encoded in the decoder and encoder circuit 60 prior to transmission. The manner of establishing and operating a telemetry link between an external programmer and implantable medical devices is known in the art.

The data instructions stored in the memory 62 control the operation of the pacemaker. In particular, the stimulation pulses generated by the pacemaker are generated in pulse output circuits 44 as triggered by appropriate trigger signals obtained from the pacemaker state logic and related circuitry 42. The state logic circuitry 42 defines a plurality of operating states for the pacemaker 16 as a function of various timing signals generated by the pacemaker timer circuits 50 and/or various other signals or conditions sensed through the atrial, ventricular, or telemetry channels of the pacemaker 16. For example, at the conclusion of an appropriate timing interval, typically referred to as the atrial escape interval, the state logic 42 changes to a particular state that causes an atrial stimulation pulse (A-pulse) to be generated by the pulse output circuits 44 and delivered to the atrium 28 through the electrode 24 via the atrial lead 31. In a similar manner, the state logic 42 changes to another particular state that causes a ventricular stimulation pulse (V-pulse) to be generated at the conclusion of another timing interval, typically referred to as the ventricular escape interval, which V-pulse is delivered to the ventricle 32 through the electrode 46 via the ventricular lead 30.

When operating in a demand mode, stimulation pulses are provided as above described only in the absence of natural cardiac activity, i.e., only when the heart 18 is not beating (contracting) on its own. Natural cardiac activity is determined by monitoring the leads 30 and/or 31 for electrical activity which the heart generates and which is indicative of muscle contraction. Atrial contraction is manifest by the presence of a P-wave sensed through the atrial tip electrode 24 and the atrial lead 31 through amplifier 48. Similarly, ventricular contraction is manifest by the presence of an R-wave sensed through the ventricular tip electrode 46 and the ventricular lead 30 through amplifier 46. Thus, the occurrence of a P-wave, for example, causes the state logic 42 to immediately assume a different state, which state restarts the atrial escape interval timer in the pacemaker timer circuits 50, and thus inhibits an A-pulse from being generated. In like manner, the occurrence of an R-wave causes the state logic 42 to assume yet another state, which state restarts the appropriate time intervals in the pacemaker timer circuits, and inhibits a V-pulse from being generated.

The physiological or other sensor 26 (usually referred to as just the "sensor") senses an appropriate non-P-wave parameter, such as physical activity, blood oxygen level, respiration rate, etc. The physiological or other parameter thus sensed is indicative of how fast the heart 18 should be beating. That is, in times of high physiological stress, such as a high physical activity level, the heart needs to beat at a much faster rate in order to provide an adequate blood supply to the patient's body. Contrariwise, in times of low physiological stress, such as a very low physical activity level (e.g., when the patient is sleeping), the heart may appropriately beat at a much slower rate. Thus, in a pacemaker programmed to operate using the physiological sensor 26, the state logic 42 receives a signal 53 generated by the sensor 26 (generally referred to as the "sensor input signal," because it is the signal that is "input" to the pacemaker 16 from the sensor 26), processes the signal 53 in an appropriate manner, and uses the processed result to alter or adjust the basic time intervals of the pacemaker so that the pacemaker will provide stimulation pulses on demand at a faster or slower rate, as needed. Such a pacemaker 16, i.e, one that is capable of adjusting the rate that stimulation pulses are provided on demand as a function of one or more sensed physiological parameters, is known as a "rate-responsive pacemaker." It is noted that the present invention has applicability to rate-responsive pacemakers, as well as non-rate-responsive pacemakers.

It is also noted that the pacemaker state logic 42, and the pacemaker timer circuits 50, while shown as separate blocks in the block diagram of FIG. 2, may be realized using a microprocessor circuit 52 controlled by an appropriate programmed set of instructions in the memory 62. In fact, the preferred manner of implementing the pacemaker 16 is to use a microprocessor 52 in combination with appropriate logic circuitry as described in U.S. Pat. No. 4,940,052, which patent is incorporated herein by reference.

In general, the states defined by the pacemaker state logic 42 may be as summarized below in Table 1. Table 1 is taken from the '052 patent, cited above, and much of the terminology used in Table 1 is further explained in that patent. Note from Table 1 that the entire operation of the pacemaker 18 for dual-chamber operation may be controlled by defining some 18 states.

TABLE 1

States of Pacemaker State Logic

| State | Symbol | Description |
|---|---|---|
| 0 | APW | A Pulse |
| 1 | BLANK | V Sense Input Inhibit (Blank) |
| 2 | AREF | A Refractory |
| 3 | SIPW | Sensed Inhibiting P Wave |
| 4 | AVD | A-V Delay |
| 5 | CROSS | Crosstalk Sense |
| 6 | VPW | V Pulse |
| 7 | SIRW | Sensed Inhibiting R Wave |
| 8 | VAD | V-A Delay |
| 9 | SHORT1 | Shorten A-V Delay 50 msec if IPW during SHORT1 with Physiologic A-V Delay On |
| A | MTR | Maximum Track Rate — Shorten |

TABLE 1-continued

States of Pacemaker State Logic

| State | Symbol | Description |
|---|---|---|
| | | A-V Delay 25/75 msec and Delay IPW until MTR end if P wave sensed during MTR; 75 msec if Physiologic A-V Delay On |
| B | SHORT2 | Shorten A-V Delay 75 msec if IPW during SHORT2 with Physiologic A-V Delay On |
| C | RRT | Lengthen V-A interval if at low battery |
| D | RNOISE | R Noise sensed during VREF or RNOISE |
| E | LIPW | Latched IPW — P wave sensed in MTR |
| F | PNOISE | P Noise sensed during AREF or PNOISE |
| (none) | VREF | V Refractory, independent 1-bit state machine synchronized to PGSL when AREF starts |
| (none) | ABSREF | 108 msec Absolute Refractory starts when AREF starts |

The External Programmer

Figure 3:
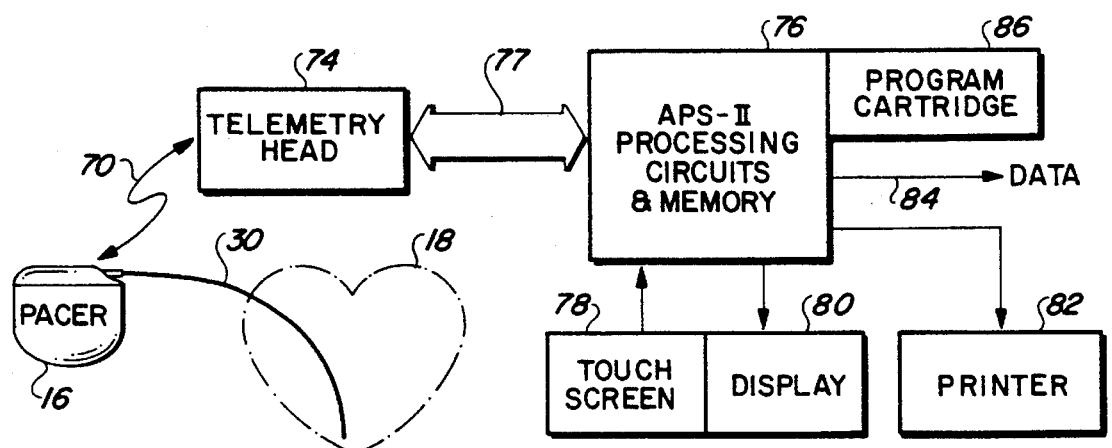
FIG. 3 is a simplified block diagram of an external programmer, referred to herein as the "APS-II/MTM," that may be used with an implantable pacemaker in accordance with the present invention.
Figure 4:
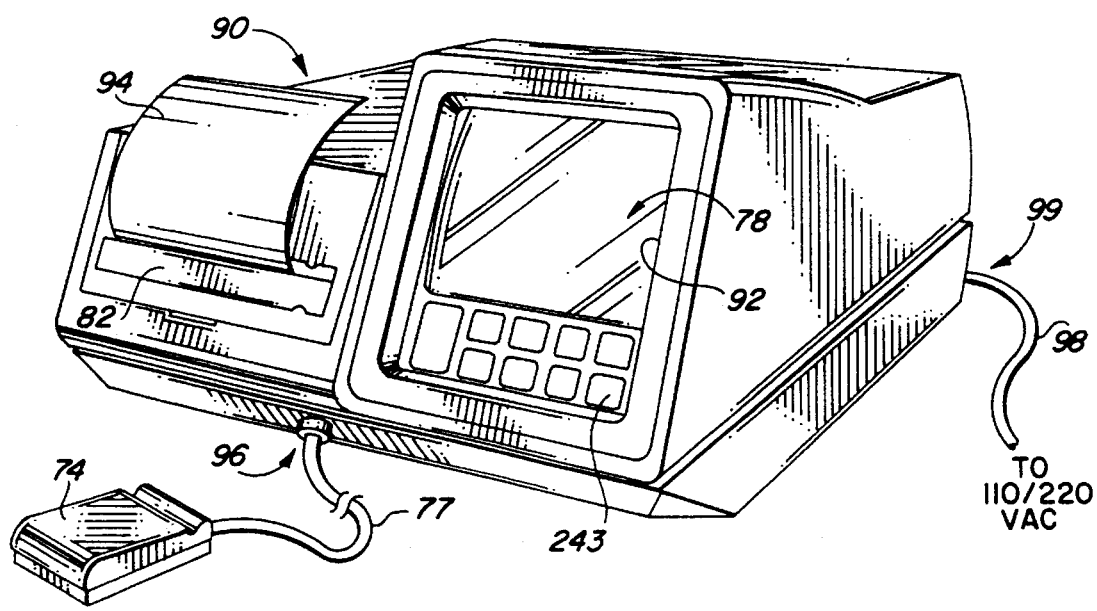
FIG. 4 is a perspective view of the APS-II/MTM external programmer of FIG. 3.

It is noted that FIGS. 1 and 2, as described above, relate primarily to the pacemaker side of a pacing system 16. However, as noted above, the external programmer side of a pacing system also plays a key part of the invention. Hence, a brief overview of the external programmer 20 used with the present invention will next be presented. Such brief overview will be made in conjunction with FIGS. 3 and 4. FIG. 3 shows a block diagram of an external programmer 20 usable as part of the present invention, while FIG. 4 shows a perspective view of the external programmer of FIG. 3. A more complete description of the external programmer 20 may be found in U.S. Pat. No. 4,809,697, which patent is also incorporated herein by reference.

The external programmer 20 used with the present invention is hereafter referred to as an analyzer-programmer system (APS). A preferred model of the APS is the APS-II/MTM, manufactured and sold by Siemens Pacesetter, Inc., of Sylmar, Calif. The APS-II/MTM provides a sophisticated, microprocessor-based programming system that can be used to noninvasively interrogate and program the programmable, implantable pacemakers manufactured by Siemens Pacesetter, Inc. However, while the APS-II/MTM represents the preferred embodiment and best mode of the programmer 20, it is to be understood that other models and types of external programmers can and will exist with which the present invention may be used. It is further noted that some of the processing and display features of the APS-II/MTM are described in U.S. Pat. No. 4,791,936, also incorporated herein by reference.

Turning to FIG. 3, it is seen that the programmable pacemaker 16, presumably implanted within living tissue, is in electrical contact with the heart 18 via at least one pacemaker lead 30. (It is noted that while the pacemaker 16 in FIG. 3 is presumed to be implanted in a patient, it need not be implanted for the APS-II/MTM to function. For example, for training purposes, it is quite common to use an APS-II/MTM with a non-implanted pacemaker that is coupled to a heart simulator.)

As described above in connection with FIGS. 1 and 2, the pacemaker 16 is a self-contained unit capable of both sensing natural cardiac activity (P-waves and/or R-waves) and providing stimulation pulses (A-pulses and/or V-pulses) to invoke paced cardiac activity. The operating characteristics of the pacemaker 16 can be noninvasively programmed by way of command signals received over telemetry link 70, which command signals are received from a telemetry head 74 connected to the APS-II/MTM processing circuits 76 by way of a connection cable 77. The command signals are generated within the APS-II/MTM processing circuits 76 as a function of operating commands received by way of a touch sensitive screen 78. That is, an APS-II/MTM operator selects a desired command by touching a designated area on the touch screen 78, which designated area is defined by a particular pattern displayed on a display screen 80. Advantageously, the touch screen 78 overlays the display screen 80 so that all one need do to make a command selection is to touch the screen at the area indicated on the display for the desired command.

The pacemaker 16 is also capable of sending operating data and measured data over the telemetry link 70 to the telemetry head 74. Such measured data includes event/rate data as described more fully below, which event/rate data is determined by monitoring particular changes in state of the pacemaker state logic 42. The telemetry head 74 preliminarily processes such data and forwards it on to the APS-II/MTM processing and memory circuits 76. Data received at the APS-II/MTM circuits 76 may be displayed on the display screen 80, printed on a printer 82, and/or stored within the memory elements of the APS-II/MTM circuits 76 for subsequent retrieval and display. Alternatively or conjunctively, data received at the APS-II/MTM circuits 76 may be transmitted over an appropriate data channel 84 to a desired external device, such as a modem, an X-Y plotter, a tape or disk drive, a personal computer, or other peripheral device.

Operation of the APS-II/MTM processing and memory circuits is controlled by way of a program cartridge 86 that is detachably connected to the processing and memory circuits 76. Removable program cartridge 86 thus advantageously allows the operating characteristics of the APS-II/MTM device to be easily upgraded to include new features and to properly interface with new pacemakers, as new features and new pacemakers are developed. Such upgrading can occur at minimal cost because all that is required is a new program cartridge 86, rather than a whole new analyzer-programming system 20, as has been required in the past. The present invention, relating to a method and system for recording and reporting the distribution of pacing events over time, is facilitated through the use of a such new program in a new program cartridge 86.

FIG. 4 illustrates a housing 90 within which the APS-II/MTM system components are housed. In accordance with one embodiment, all of the circuits of the APS-II/MTM processing circuits and memory 76, including the printer 82, the display screen 80, the touch screen 78, and the program cartridge 86, are housed within the housing 90. The telemetry head 74 is coupled to the housing 90 by way of cable 77. As seen in FIG. 4, a CRT screen 92, over which touchscreen 78 is laid, provides a readily visible and accessible means for viewing displays and selecting commands. Similarly, the printer 82 provides a paper copy 94 of that which is displayed on the screen of the CRT 92, or other desired information, as selected by the various commands available through touching the touchscreen. The telemetry head module 74 is attached to cable 77 which plugs into a connector 96 located on the bottom front side of the housing 90. A power cord 98 similarly plugs into socket 99 at the rear of the housing and allows the APS-II/MTM to be powered from any suitable electrical outlet providing 110/120 VAC at 60 Hz. The power cord 98 may be stored on the bottom of the housing 90 for ease of transportation and storage. Similarly, the telemetry head 74, when detached, can be stored in a removable front cover (not shown) when not in use.

Gathering the Event Record Data

Figure 5:
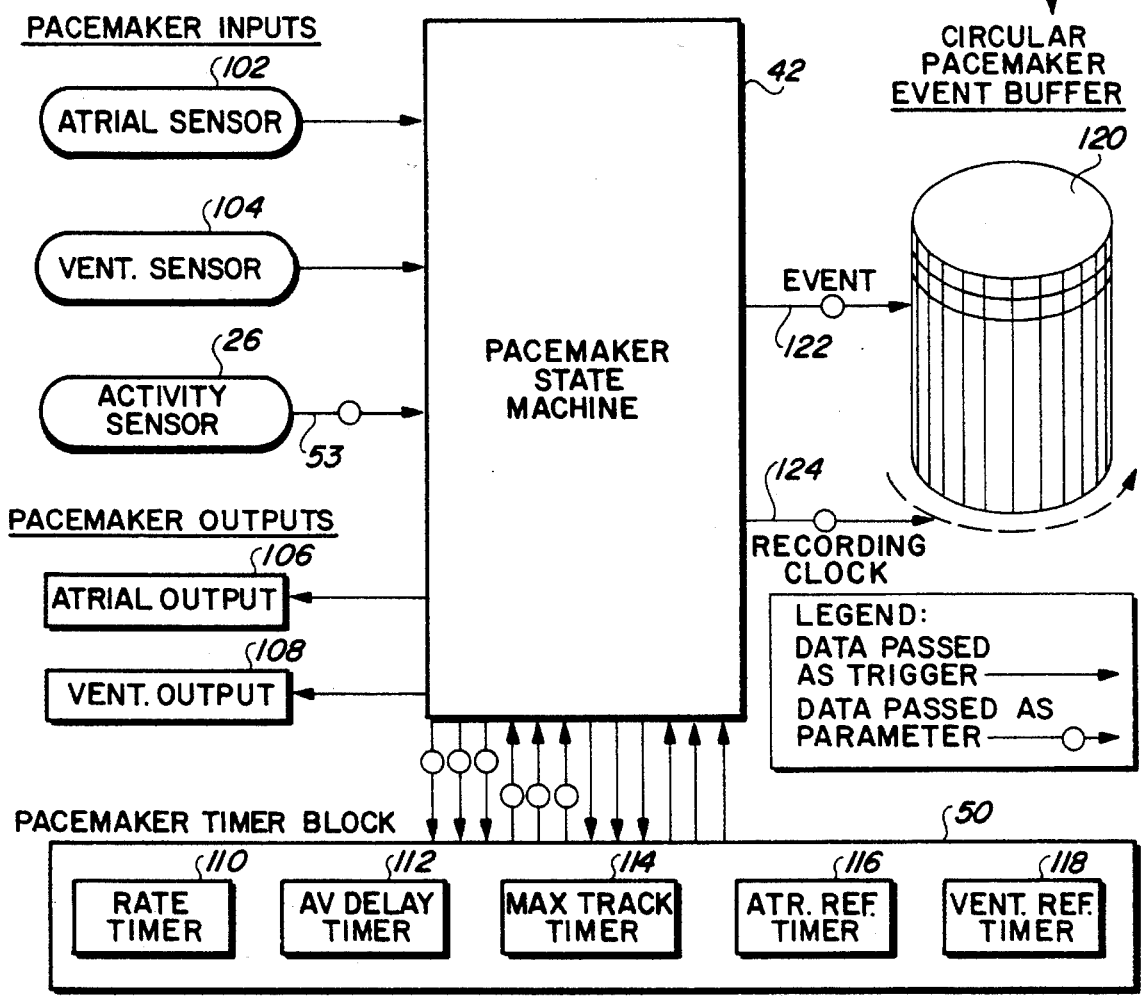
FIG. 5 is a functional block diagram of the pacemaker of FIG. 2, showing a "circular" buffer into which an Event Record is stored as specified pacing events occur as determined from examining the state of the pacemaker state machine.

With the above overview in mind of both the pacemaker 16 and the external programmer 20 of a representative pacing system, reference is next made to FIG. 5 where there is shown a functional block diagram of the pacemaker 16 that highlights the key elements used with the present invention. As with all the figures used herein, like reference numerals are used in FIG. 5 to describe like parts used in other figures. Thus, shown in FIG. 5 is the pacemaker state logic 42, referred to as the pacemaker state machine. Also shown in FIG. 5 is the pacemaker timer circuits 50, referred to as the pacemaker timer block. The pacemaker inputs, i.e., signals sensed by the pacemaker that are not programmed, include an atrial sensor 102 and a ventricular sensor 104 that sense P-waves and R-waves, respectively. For example, the atrial sensor 102 may be made up of the atrial tip electrode 24, atrial lead 31 and atrial channel amplifier 48 as shown in FIG. 2. Similarly, the ventricular sensor 104 may be made up of the ventricular tip electrode 46, the ventricular lead 30 and the ventricular amplifier 56 shown in FIG. 2. The pacemaker inputs also include the sensor input signal 53 obtained from the physiological sensor 26. (It is noted that while only a single physiological sensor 26 is shown in FIGS. 1, 2 and 5, more than one such sensor may be used, each providing its own sensor input.)

In addition to the above-described pacemaker inputs, there are several pacemaker parameters that are input to the pacemaker state machine in order to control its operation in a desired fashion. Such parameters are normally programmed into the memory 62 of the pacemaker 16 using the appropriate telemetry link 70. Such parameters include, e.g., the programmed rate at the which the stimulation pulses are to be generated by the pacemaker, the particular mode of operation of the pacemaker, and the like.

The pacemaker outputs, i.e., signals generated by the pacemaker state machine 42 in response to the pacemaker inputs and/or pacemaker parameters include an atrial output 106 and a ventricular output 108. The atrial output 106 provides an A-pulse for delivery to the atrium at an appropriate time, e.g., on demand as needed to maintain a programmed or sensor-indicated heart rate. The ventricular output 108 similarly provides a V-pulse for delivery to the ventricle at an appropriate time, e.g., on demand as needed to maintain a programmed or sensor-indicated heart rate.

The pacemaker timer circuits 50 include at least five separate timers. A rate timer 110 determines or measures the pacing cycle duration. An AV Delay Timer 112 defines the time period between an A-pulse and a V-pulse. A Max Track Timer 114 defines the time period of the maximum rate at which the pacemaker is allowed to provide stimulation pulses, i.e., it defines the maximum paced rate. An Atrial Refractory Timer 116 defines the atrial refractory period (i.e., that time period during which the atrial channel is refractory). Similarly, a Ventricular Refractory Timer 118 defines the ventricular refractory period, or that time during which the ventricular channel is refractory.

Note from the symbols used in FIG. 5 that two kinds of data are passed to and from the pacemaker state machine 42. Such data may take the form of a trigger signal or a parameter signal. A trigger signal, represented by an input line with an arrow pointing the direction of flow of the trigger data, is a signal that operates substantially immediately, much like an interrupt signal, to bring about a desired result. That is, for example, immediately upon sensing atrial activity through the atrial sensor (or within one or two clock cycles thereafter, where a clock cycle is typically on the order of a few microseconds), the state of the state machine 42 changes appropriately to bring about a desired result. In contrast, a parameter signal, represented by an input line passing through a circle with an arrow pointing the direction of flow of the parameter data, is a signal that is made available to the indicated element for use at the appropriate time during the normal timing cycle of the state machine.

As indicated above in Table 1, there are some eighteen states associated with the operation of the pacemaker 16 when configured for operation in a dual-chamber mode. Three of the eighteen defined states relate directly to cardiac activity that occurs in the atrium. These three atrial states are: (1) atrial pulse (A-pulse), referred to as "APW" or state 0 in Table 1; (2) sensed P-wave, referred to as "SIPW" or state 3 in Table 1; and (3) sensed P-wave during the Maximum tracking interval, referred to as "LIPW," or state E in Table 1. Similarly, two of the eighteen defined states relate to cardiac activity that occurs in the ventricle. These two ventricle states are: (1) ventricular stimulation pulse (V-pulse), referred to as "VPW," or state 6 in Table 1; and (2) sensed R-wave, referred to as "SIRW," or state 7 in Table 1. Advantageously, the changing of the state machine 42 from one state to another state signals the occurrence of a particular event. Selected state changes associated with the state machine 42 may thus be considered as "pacing events." Such pacing events may also be considered as one of the outputs of the state machine 42, and such events are identified generically in FIG. 5 as a data parameter 122. In accordance with the present invention, such pacing events are recorded in sequence as they occur, or at a specified sampling rate, and as a function of the type and rate of event that occurred in a "circular" buffer memory 120. Note that a "circular" buffer memory is simply a designated portion of the pacemaker memory 62 wherein the data parameters are stored in such a way that they can be retrieved in the same order in which they were stored, and wherein the newest or most recent data always replaces the oldest or least recent data. Thus, the circular buffer memory 120 always contains the last n pacing events stored therein, where n is the storage capacity of the circular buffer memory 120.

There are four basic pacing event types that are recorded by the present invention. These are: (1) a P-wave followed by a V-pulse (referred to as a "PV" event); (2) a P-wave followed by an R-wave (referred to as a "PR" event); (3) an A-pulse followed by a V-pulse (referred to as an "AV" event); and (4) an A-pulse followed by an R-wave (referred to as an "AR" event). Note from Table 1 that a PV event occurs when the state machine 42 changes from state 3 to state 6. Similarly, a PR event occurs when the state machine changes from state 3 to state 7; an AV event occurs when the state machine changes from state 0 to state 6; and an AR event occurs when the state machine changes from state 0 to state 7.

To the above four basic pacing event types, three other pacing events may be defined. These other three pacing event types are: (5) a premature ventricular event (referred to as a "PVE"); (6) a P-wave at the maximum tracking rate followed by a V-pulse (referred to as a "P@MTR-V" event); and (7) a P-wave at the maximum tracking rate followed by an R-wave (a "P@MTR-R" event). A premature ventricular event is defined as an R-wave that occurs without an appropriate preceding atrial event. With respect to the states defined in Table 1, a PVE may thus occur when the state machine 42 changes from state 8 (which may be initiated after state 6 or state 7) back to state 7. (In a non-PVE sequence, state 8 would normally be followed by state 0 or state 3.) A P@MTR-V event occurs when the state machine changes from state E (LIPW) to state 6 (VPW). Similarly, a P@MTR-R event occurs when the state machine changes from state E to state 7 (SIRW). For most purposes related to the Event Record of the present invention, a P@MTR-V event may be considered as a PV event; and a P@MTR-R event may be considered as a PR event.

In addition, a "magnet" event occurs when a magnet is placed over the device, either singly or in conjunction with the telemetry system. Use of a magnet to mark an event will be discussed below.

It is noted that if only single-chamber pacing is employed, then the pacing events that are detected and recorded in the Event Recorded are simply "sensed events" and "paced events."

Because the pacing events defined above are reflected in prescribed state changes of the state machine 42, the occurrence of such events can be readily determined by monitoring the state machine for the prescribed state changes. In particular, in accordance with the present invention, and as indicated above, the occurrence of any of the above-defined seven pacing events is stored in a circular buffer memory 120, as shown in FIG. 5. As the pacing events are stored, they are stored as an Event Sample data word having at least two fields. A first field identifies the pacing event type. A second field identifies the pacing event as belonging to one of a plurality of rate ranges, as explained more fully below.

Appropriate circuitry within the pacemaker 16, and particularly within the memory 62 of the pacemaker 16, stores the pacing event data in the proper sequence and with the proper event designator and rate fields. In applicants' preferred embodiment, 4096 bytes of the pacemaker memory 62 are allocated for the storage of the Event Record data. However, this number of storage bytes is only exemplary. Typically, at least 4000 bytes of storage should be provided, with much more being provided if available.

Appropriate commands received from the external programmer 20 allow the Event Record data to be downloaded to the external programmer. A two-bit code held in a designated location of the memory 62 specifies whether the sampling rate is every event (code 00), every 1.6 seconds (code 10), or every 26 seconds (code 10). The sampling rate thus defines the Event Record sampling period, as represented by the "recording clock" 124 in FIG. 5. At the end of each sampling period, i.e., as controlled by the recording clock 124, a new Event Sample is stored in the Event Record Memory. If the Sampling Rate is set to "Every Event," then the sampling period becomes the event's cycle interval, meaning the recording clock has an appropriate cycle time coincident with each paced or sensed event, and a new event is stored at the end of each paced or sensed event.

The Event Sample data word 122 stored in the buffer memory 120 consists on one byte (8 bits). As previously indicated, each event sample byte includes two fields. A first field, bits 0–2, contains the Event Type Designator. Event Designators are 3-bit values in the range of 0–7 which represent each Event Type. The Event Type designators for the pacing events monitored by the present invention are defined in Table 2.

TABLE 2

| EVENT DESIGNATOR | |
| --- | --- |
| Event Type | Event Designator |
| AV | 0 (000) |
| AR | 1 (001) |
| PVE | 2 (010) |
| PV | 3 (011) |
| PR | 4 (100) |
| P@MTR-V | 5 (101) |
| P@MTR-R | 6 (110) |
| MAGNET | 7 (111) |

The second field in each Event Sample 122 is bits 3–7. This field contains the cycle time. The cycle times are 5-bit values in the range of 0–31 that represent the pacing cycle time corresponding to each pacing event. The lowest Cycle Time value of 0 represents a pacing interval of approximately 323.7 msec (or 185.3 ppm). Each successive value increments the interval by approximately 25.3 msec. The highest value of 31 represents 1110.8 msec (or 54 ppm). Table 3 lists the interval time for each cycle time value.

TABLE 3

| Event Record Cycle Times | | |
| --- | --- | --- |
| Bin No. | Range, MSec | Range, PPM |
| 0 | 323.7–342.8 | 185.3–175.0 |
| 1 | 349.1–368.2 | 171.9–163.0 |
| 2 | 374.5–393.6 | 160.2–152.5 |
| 3 | 399.9–418.9 | 150.0–143.2 |
| 4 | 425.3–444.3 | 141.1–135.0 |
| 5 | 450.7–469.7 | 133.1–127.7 |
| 6 | 476.1–495.1 | 126.0–121.2 |
| 7 | 501.5–520.5 | 119.6–115.3 |
| 8 | 526.9–545.9 | 113.9–109.9 |
| 9 | 552.2–571.3 | 108.6–105.0 |
| 10 | 577.6–596.7 | 103.9–100.6 |
| 11 | 603.0–622.1 | 99.5–96.5 |
| 12 | 628.4–647.5 | 95.5–92.7 |
| 13 | 653.8–672.9 | 91.8–89.2 |
| 14 | 679.2–698.2 | 88.3–85.9 |
| 15 | 704.6–723.6 | 85.2–82.9 |
| 16 | 730.0–749.0 | 82.2–80.1 |
| 17 | 755.4–774.4 | 79.4–77.5 |
| 18 | 780.8–799.8 | 76.8–75.0 |
| 19 | 806.2–825.2 | 74.4–72.7 |
| 20 | 831.5–850.6 | 72.2–70.5 |
| 21 | 856.9–876.0 | 70.0–68.5 |
| 22 | 882.3–901.4 | 68.0–66.6 |
| 23 | 907.7–926.8 | 66.1–64.7 |
| 24 | 933.1–952.1 | 64.3–63.0 |
| 25 | 958.5–977.5 | 62.6–61.4 |
| 26 | 983.9–1002.9 | 61.0–59.8 |
| 27 | 1009.3–1028.3 | 59.4–58.3 |
| 28 | 1034.7–1053.7 | 58.0–56.9 |
| 29 | 1060.1–1079.1 | 56.6–55.6 |
| 30 | 1085.4–1104.5 | 55.3–54.3 |
| 31 | 1110.8–1129.9 | 54.0–53.1 |

Figure 7:
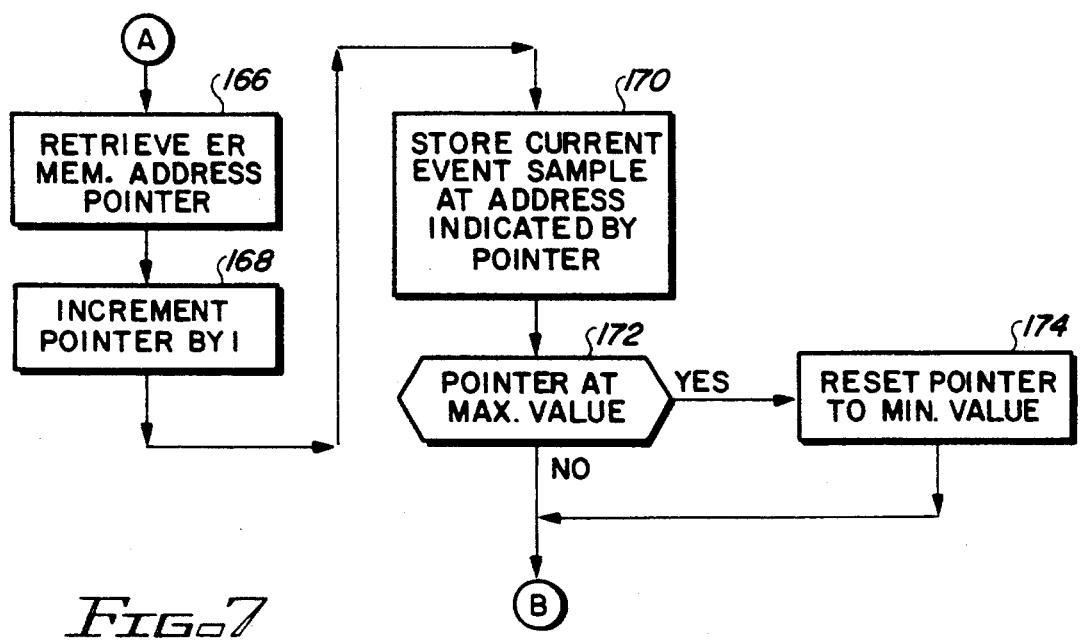
FIGS. 6 and 7 are flowcharts depicting the manner in which pacing events are detected and stored in the circular buffer within the pacemaker.
Figure 6:
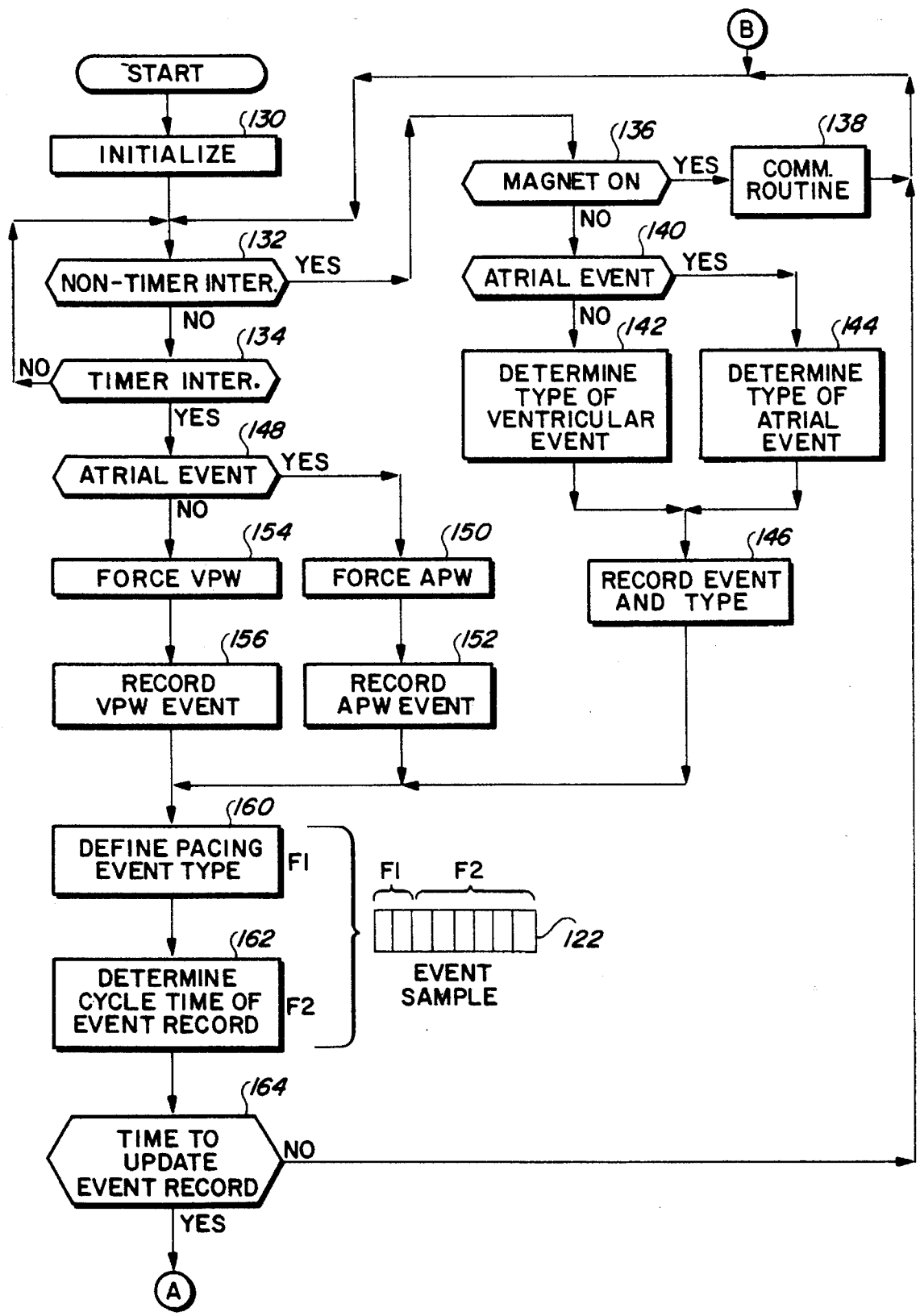

Turning next to FIGS. 6 and 7, there is shown a flowchart that depicts the manner in which the Event Sample data words are stored in the buffer memory 120. In FIGS. 6 and 7, each main program step is referred to as a "block," with a reference numeral being assigned to each block for identification purposes.

Referring to FIG. 6, a first step of the process is to perform appropriate initialization steps, such as setting various variables, clearing or setting registers, and the like (block 130). Once the initialization has occurred, a determination is made as to whether a non-timer interrupt is present (block 132), i.e, whether a natural cardiac event, such as an R-wave or a P-wave has been sensed. If not, then a next determination is made as to whether a timer interrupt is present (block 134), i.e, whether an applicable escape interval or other pacemaker-defined interval, has timed out. If not, then the program control loops back to block 132, and the process continues. In other words, the main branch of the program for the processor 52 of the pacemaker 16, or equivalent state logic circuitry, is to wait for an interrupt signal to be received either from an non-timer source, or a timer source.

If an interrupt is received from a non-timer source, then the appropriate timers are reset or restarted, and a determination is made as to whether the magnet is on (block 136). The magnet is on when the telemetry head 74 of the external programmer 20 is placed in position to establish the telemetry link 70 between the pacemaker 16 and the external programmer. (In addition, a magnet may be used by the patient to mark an event.) Thus, if the magnet is not on, that indicates the external programmer is not present, and in such instance a determination is then made as to whether the non-timer interrupt signal is related to an atrial event, e.g., an LIPW, SIPW or APW (block 140). See Table 1 for a definition of these terms. If so, then a further determination is made as to the type of atrial event (block 144), which determination is easily made by monitoring the state of the state machine. If the event is not an atrial event (block 140), then that indicates the event must be a ventricular event (SIRH or VPW), and an appropriate event type is defined (block 142). The occurrence of such events is recorded (block 146) in a temporary buffer or latch register. Also recorded is a corresponding indication of the cardiac/pacing cycle associated with such event. The cardiac/pacing cycle is determined or measured by the rate timer 110 (see FIG. 5), and provides an indication of the current pacing rate. Typically, the rate timer 110 measures the time period between successive ventricular events, V-pulses or R-waves; although if may also be configured to measure the time between successive atrial events, P-waves or A-pulses.

If the magnet is on (block 136), then that indicates the telemetry head of the external programmer is in place, and an appropriate communication routine is invoked (block 138) to establish the telemetry link 70 and to allow data to be transferred from the pacemaker, or to allow control parameters to be transferred to the pacemaker.

If an interrupt is received from a timer source (block 134), then a determination is made as to the type of interrupt (block 148). If the event is an atrial event, then an A-pulse is generated by forcing the APW state (block 150). Such APW event is recorded (block 152) in a temporary buffer register. If the event is not an atrial event, then a V-pulse is generated by forcing the VPW state (block 154). Such event is also recorded in a temporary buffer (latch) register (block 156). In this manner, one or more temporary buffer registers function as a latch circuit that keeps a temporary record of the last n events that have occurred, where n is at least two, including the pacing/cardiac cycle time associated with such events.

From the information held in the temporary buffer registers, as above described, the Event Designator is defined as a first field F1 of an Event Sample word 122 (block 160). See Table 2 for a definition of the Event Designators that are used. Also, the Cycle Time associated with the Event Sample 122 is defined as a second field F2 (block 162). See Table 3 for a definition of the Cycle Times that are used. If it is time to update the Event Record (block 164), as determined by the programmed Sampling Rate, then the Event Sample 122 is stored in the buffer memory 120 as shown in FIG. 7. If it is not time to update the Event Record (block 164), then the program loops back to the main wait loop (blocks 132, 134), and the Event Sample stored in the temporary buffer resisters will be replaced with the next Event Sample associated with the next pacing cycle.

As shown in FIG. 7, if it is time to update the Event Record (as determined at block 164 of FIG. 6-1), which time may be either every event, every 1.6 seconds, or every 26 seconds, as determined by the programmed Sampling Rate, then an address pointer is retrieved (block 166), or otherwise accessed, from a designated memory location and is incremented by one (block 168). The address pointer is a 16 bit word stored in two bytes of memory. The current Event Sample 22 is then stored at the address indicated by the address pointer (block 170). A determination is then made if the pointer is at its maximum value (block 172), and if so, the pointer is reset to its minimum value (block 174). In this instance, the buffer memory consists of 4096 memory locations, each having a capacity of one byte. Thus, 4096 Event Samples can be stored, with the address pointer always pointing to the address of the next location. Thus, the memory 120 is accessed as a circular buffer. The most recent Event Sample stored in the Event Record memory 120 is stored at the address indicated by the address pointer. This has the effect of overwriting the oldest Event Sample in the Event Record Memory 120 with the newest Event Sample. As described above, it is thus seen that if the buffer memory 120 has a capacity for storing n Event Sample data words, where n is an integer, each of the Event Sample data words stored in the buffer memory are arranged in an ordered sequence so that the (n+1)th Event Sample data word stored in the buffer memory replaces the 1st Event Sample data word stored in the buffer memory, the (n+2)nd Event Sample data word stored in the buffer memory replaces the 2nd Event Sample data word stored in the buffer memory, and so on, with the (n+i)th Event Sample data word stored in the buffer memory replacing the ith Event Sample data word stored in the buffer memory, where i is also an integer. Thus, the most recent Event Sample data word stored in the buffer memory always replaces the oldest Event Sample data word stored in the buffer memory, and the buffer memory contains the n most recent Event Sample data words.

It is noted that the Sampling Rate is a programmed parameter that is sent to the pacemaker memory 62 in response to a specific request and explicit confirmation. Note also that, unlike Sensor and Event Histogram data that may be stored and cleared in other locations of the pacemaker memory 62, the Event Record cannot be cleared in the current preferred embodiment. However, it may be useful to allow the Event Record to be cleared for certain applications. Moreover, the Event Memory 120 and the Event Sample Pointer (address pointer) cannot be written to by the APS-II/MTM programmer.

It should also be pointed out that the monitored pacing events that are stored in the circular buffer memory 120, are also counted in appropriate pacemaker event counters as a function of rate of occurrence to create pacing event/rate data useful in the generation of an Event/Rate Histogram. The gathering, processing and display of such event/rate data is described in commonly owned U.S. Pat. No. 5,309,919, granted May 10, 1994, entitled METHOD AND SYSTEM FOR RECORDING, REPORTING, AND DISPLAYING THE DISTRIBUTION OF PACING EVENTS OVER TIME AND FOR USING SAME TO OPTIMIZE PROGRAMMING, which patent is incorporated herein by reference.

Thus it is seen that the pacemaker has reserved 4096 bytes of storage space for the Event Record. Each byte in this storage contains the event type and rate information. There are eight different possible event types and 32 rate categories. The event types require 3 bits, and the rate category requires 5 bits, making a total of eight bits per byte.

It is also seen that a processor 52 incorporated into the pacemaker 16 tracks the pacemaker state machine 42. When an event occurs, the processor determines the event type. If the sampling rate is Every Event, the appropriate Event Record is stored, based on the rate and event type. If the 1.6 second or 26 second sampling rate is programmed, the event is latched so that when the sampling interval timer expires, the appropriate Event Sample can be stored in the Event Record.

As further seen from the above, Event Sample data is accumulated continuously by the pacemaker 16 (under control of the processor 52, or equivalent circuitry), provided the system is not suspended due to the presence of a magnet. Data in the Event Record is generally never cleared, but is accumulated in a circular buffer so that the most recent collected data always overwrites the oldest collected data.

As with any programmable implantable pacing device, it is the programmed parameters of the pacemaker that influence the event types and rates that are recorded. The interaction between the pacemaker timers, the maximum intervals, and the intrinsic activity of the patient's heart ultimately determine the device behavior, and thus the data collected in the Event Record.

Processing/Displaying the Event Record Data

With the Event Record data stored in the circular buffer memory 120 of the pacemaker 16, it remains to selectively download such data so that it can be processed and displayed. Such downloading is accomplished through the telemetry link 70 established by the external programmer 20. Advantageously, by using the APS-II/MTM processing circuits and memory as controlled by an appropriate processing program stored in the program cartridge 86, the Event Record data can be displayed and printed in various graphical formats. Further, statistical data associated with the Event Record data can be computed.

It is noted that the data processing functions carried out by the APS-II/MTM programmer, as far as computing statistical information relative to the Event Record data, is straightforward. That is, there is nothing very sophisticated about the Event Record data. It is simply an indication of the most recent pacing events, and their associated pacing rates, recorded at the programmed sampling rate, in the sequence in which the event occurred. Thus, processing such data to determine, e.g., an average rate, or to determine a maximum or minimum rate, or to display the data in the sequence in which it occurred, is a straightforward process. However, the manner and format in which the Event record data is displayed can have a significant impact on how useful the data is to the physician or other medical personnel in understanding the operation of the pacemaker for a particular patient.

Advantageously, the Event Record data is accessible at any time by an external programmer through the use of an appropriate telemetry link. The preferred communication technique is to use RF telemetry, modulating the data using phase shift keying telemetry, as is described, e.g., in U.S. Pat. No. 4,944,299, which patent is incorporated herein by reference. The Event Record data can be read and reread as many times as is desired, as it is never cleared, although it is continuously updated (unless a magnet is present, in which case data collection is suspended until the magnet is removed).

The APS-II/MTM reads the Event Record data as 128 blocks of 32 bytes each. The data is then formatted for display by grouping events into time slots determined by the total time to be displayed (time scale) on the Event Record screen.

To present the data to the user, the processed Event Record data are displayed and optionally printed by the APS-II/MTM. The time scale of the display may be adjusted to view all or part of the total Event Record. With large time scales selected, events are displayed as multiple average samples, showing a range of rates as a line extending from a maximum to a minimum rate, with tick marks on the lines being used to indicate the average rate. Individual events can also be displayed by selecting a smaller time scale. The time window determined by the selected scale forms a window into the complete Event Record. Such window can advantageously be scrolled left or right to allow a specific period within the Event Record to be displayed.

In addition, the Event Record data are processed into various histograms. Statistical analysis is applied to the selected display window, or to the complete Event Record as selected. Four possible statistical graphs that show various views of the data distribution with respect to event type, event rate, and recording time are selectively provided: (1) the Event Bar Graph; (2) the Event Time Graph; (3) the Rate Bar Graph; and (4) the Rate Time Graph. Examples of such statistical graphs are described below.

Figure 8:
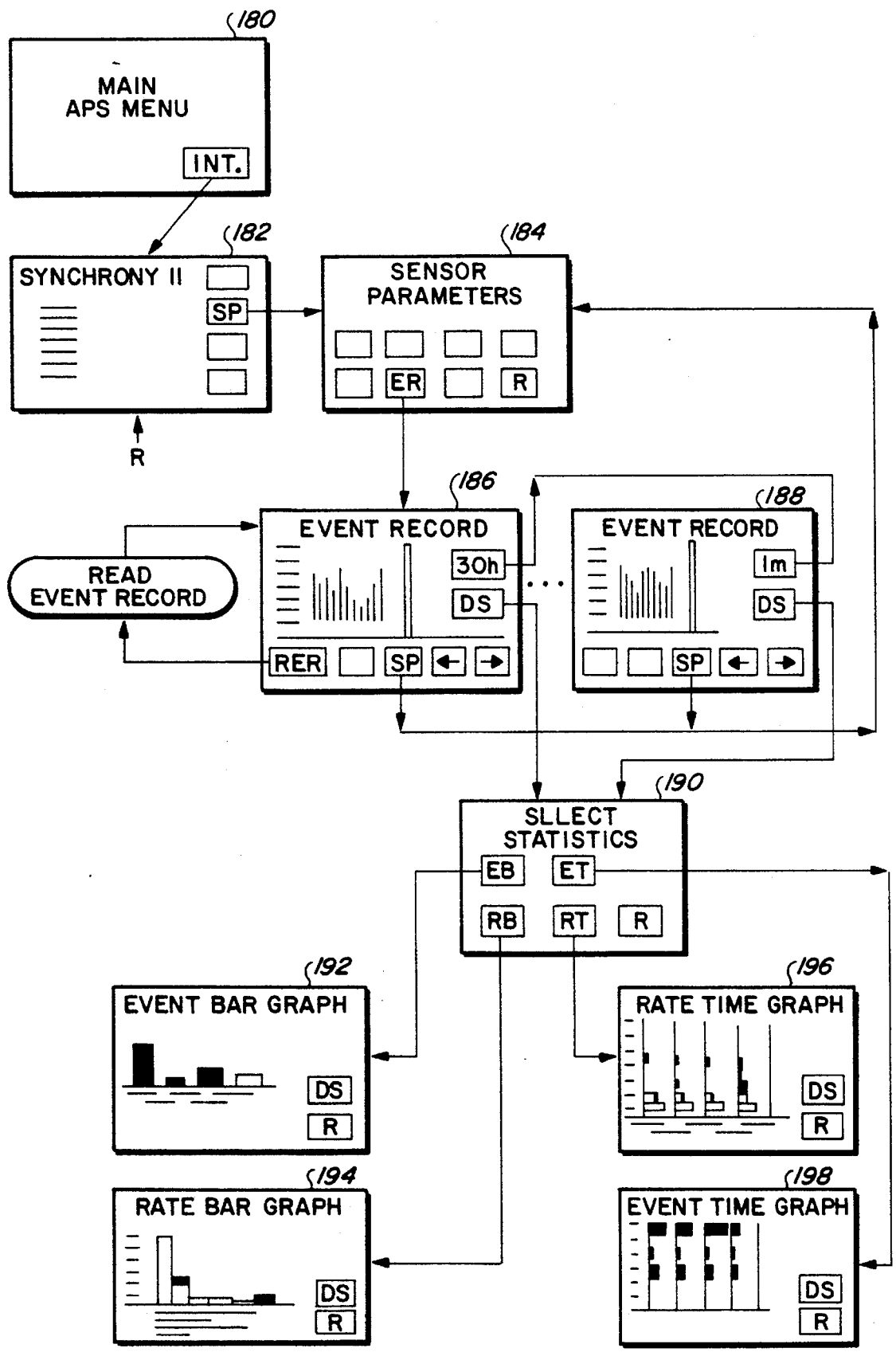
FIG. 8 is a screen display flowchart that maps the relationship between the main screen displays generated by the external APS-II/MTM programmer as it displays the Event Record in various formats.

To illustrate the manner and various formats in which the Event Record data may be displayed, reference is next made to FIG. 8 where there is shown a screen display flowchart that maps the relationship between the main screen displays generated by the external APS-II/MTM programmer 20 as it displays the Event Record in various formats. When the APS-II/MTM programmer is first turned on, a main menu screen 180 is displayed. This main menu screen allows the user to select "Interrogate" as a command in order to establish the appropriate telemetry link with the pacemaker. In response to selecting "Interrogate," a telemetry link is established between the APS-II/MTM programmer and the pacemaker. The pacemaker downloads identifying information about the pacemaker, such as its model number and serial number, as well as the current set of programmed parameters that reside in the pacemaker. Such information is displayed in a Data Display screen 182.

Several icon "buttons" are displayed along one side of the Data Display screen 182 that provide the user additional options relative to using the APS-II/MTM to interrogate and program the pacemaker. For purposes of the present invention, one of these "buttons" is a "Sensor Parameter" button. If the Sensor Parameter button is pressed (meaning if the icon representing the button is touched), then a Sensor Parameter Screen 184 is displayed. The Sensor Parameter Screen includes several additional "buttons" that provide the user with still further options. The number of selections possible from the Sensor Parameter screen 184 is a function of the particular pacemaker that is being interrogated. For the Synchrony and Solus line of pacemakers manufactured by Siemens Pacesetter, Inc. there are nine such buttons displayed: "Auto-Set"; "Sensor Param. RTS"; "Reset Auto Threshold"; "Event Histogram"; "Event Record"; "Sensor Histogram"; "Batch Store"; "Program"; and "Return." Pressing the "Event Histogram" button invokes an Event Histogram routine that is described in the above-cited patent application. Pressing the "Auto-Set" button invokes yet an additional routine, described in U.S. Pat. No. 5,292,341, granted Mar. 8, 1994, entitled METHOD AND SYSTEM FOR DETERMINING AND AUTOMATICALLY ADJUSTING THE SENSOR PARAMETERS OF A RATE-RESPONSIVE PACEMAKER, also incorporated herein by reference. Pressing the "Reset Auto Threshold" button invokes still an additional routine, described in U.S. Pat. No. 5,423,867, granted Jun. 13, 1995 entitled RATE-RESPONSIVE PACEMAKER RAVING AUTOMATIC SENSOR THRESHOLD WITH PROGRAMMABLE OFFSET also incorporated herein by reference. Pressing the "Return" button on the Sensor Parameter screen 184, or any other screen, returns the screen display to the Data Display screen 182 for the particular pacemaker being interrogated.

Figure 9:
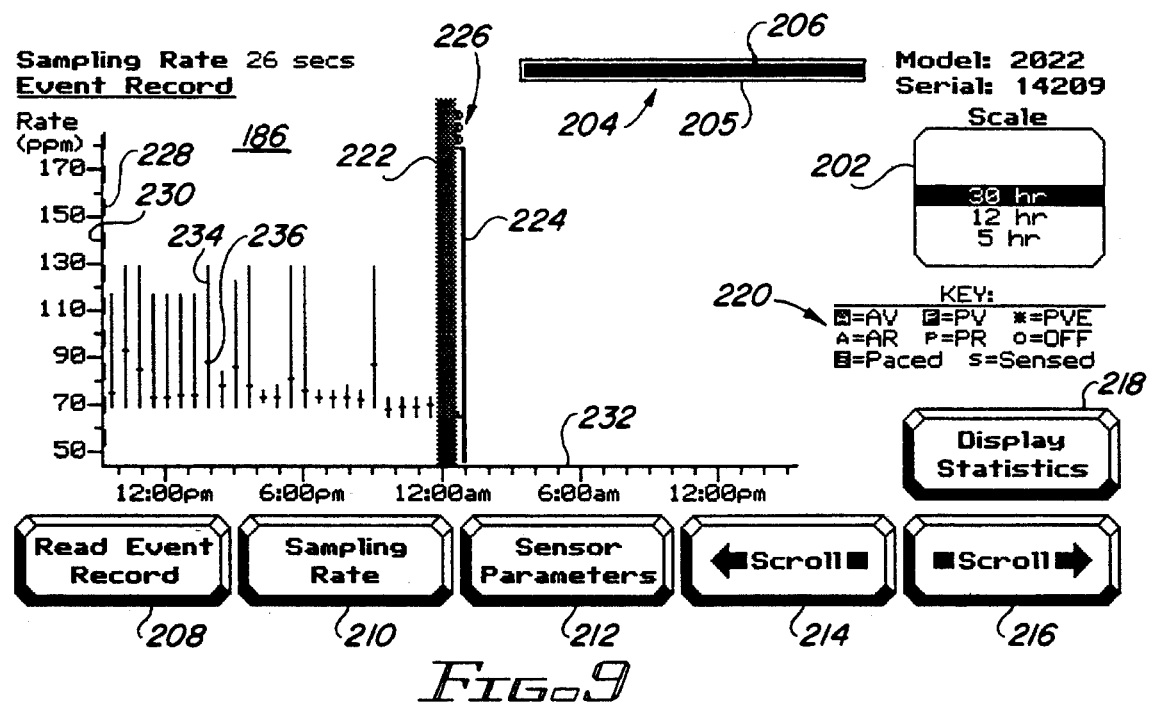
FIG. 9 is a typical Event Record screen as displayed on the APS-II/MTM external programmer with a 30 hour scale, showing multiple sample data points within a common time slot as a vertical line, with a tick mark on each line indicating the average rate.
Figure 10:
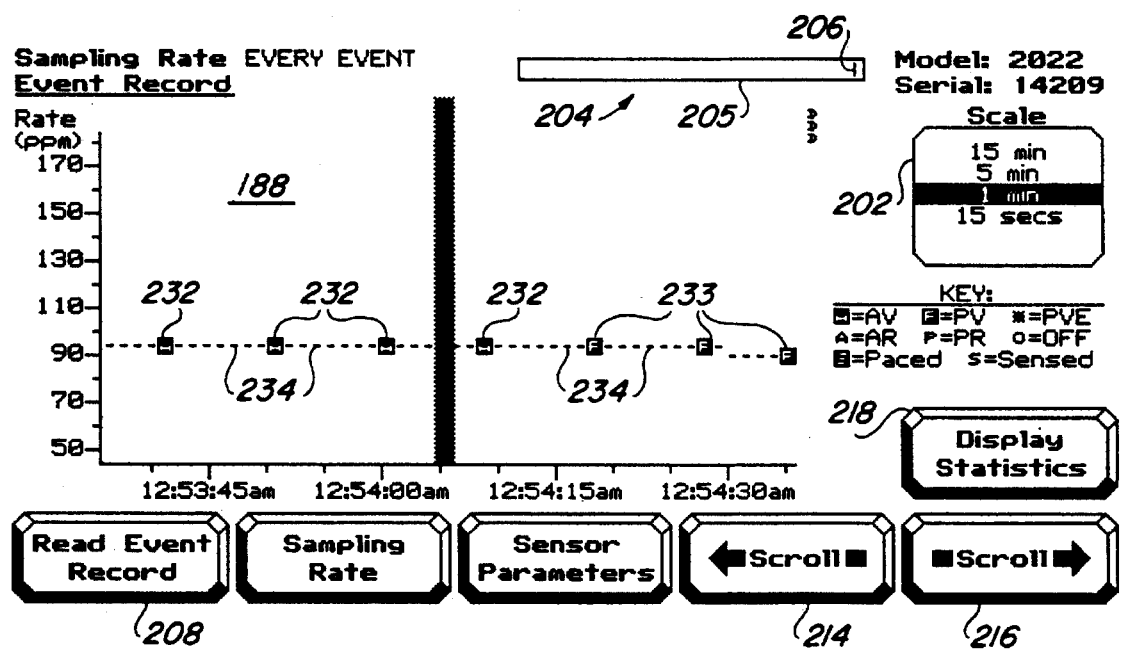
FIG. 10 is a typical Event Record screen as displayed on the APS-II/MTM external programmer with a 1 minute scale, showing single event data points in sequence.

If the "Event Record" (ER) button on the Sensor Parameter screen is pressed, then an Event Record screen 186 or 188 is displayed. If Event Record data has been read from the pacemaker buffer memory 120, then such data will be reflected in the Event record screen. If Event Record data has not been read, then the "Read Event Record" button may be pressed to effectuate such reading. Representative examples of an Event Record screen are shown in FIGS. 9 and 10.

Initially, the entire Event Record is displayed in the Event Record screen, however, by adjusting the time scale of the display, that which is displayed on the Event Record screen—the "display window"—may look at selected portions of the Event Record.

Figure 12:
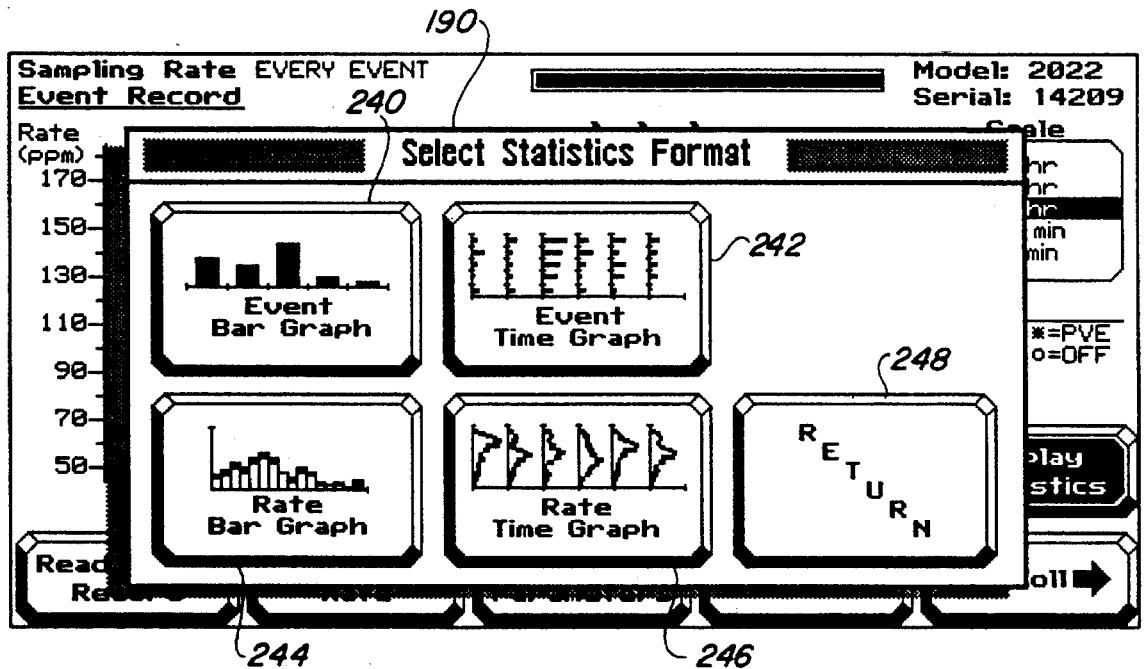
FIG. 12 shows the Select Statistics Format screen that is displayed whenever the "Display Statistics" button is pressed on the Event Record screen.

A series of icon "buttons" appear on the screen. One of these buttons is the "Read Event Record" button, referenced above. Another is the "Display Statistics" button. If the "Display Statistics" button is pressed, then a Select Statistics screen 190 is displayed. A representation of the Select Statistics screen is shown in FIG. 12.

Figure 15:
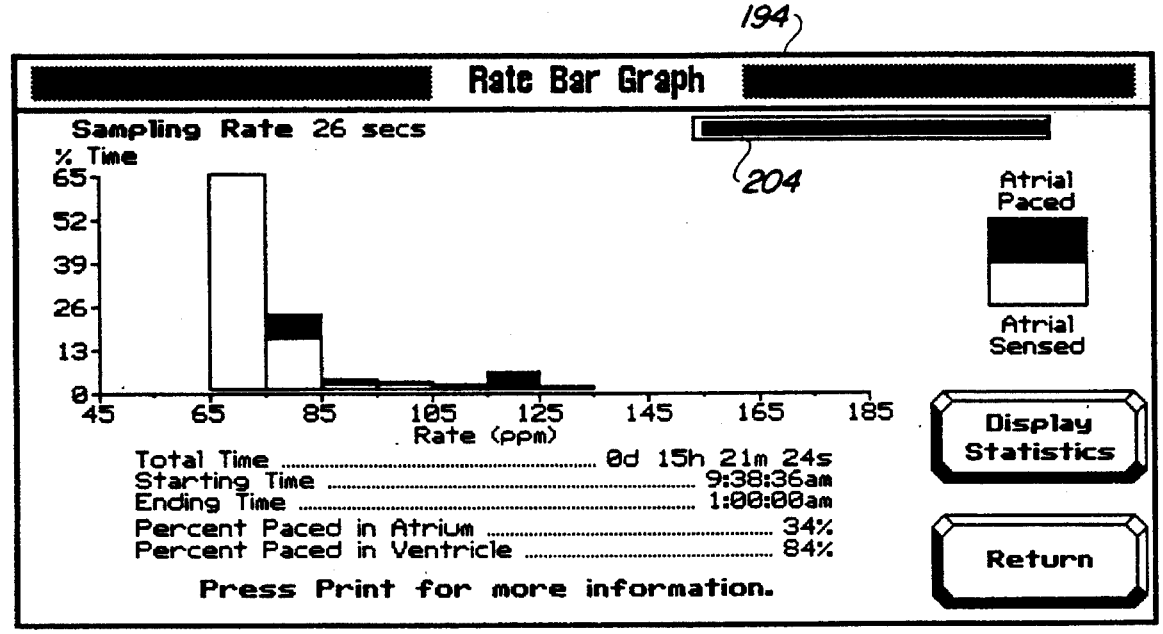
FIG. 15 shows a Rate Bar Graph screen as displayed by the APS-II/MTM programmer showing typical histogram statistical summaries of the Event Record data as a function of rate, and per cent of time paced or sensed.
Figure 16:
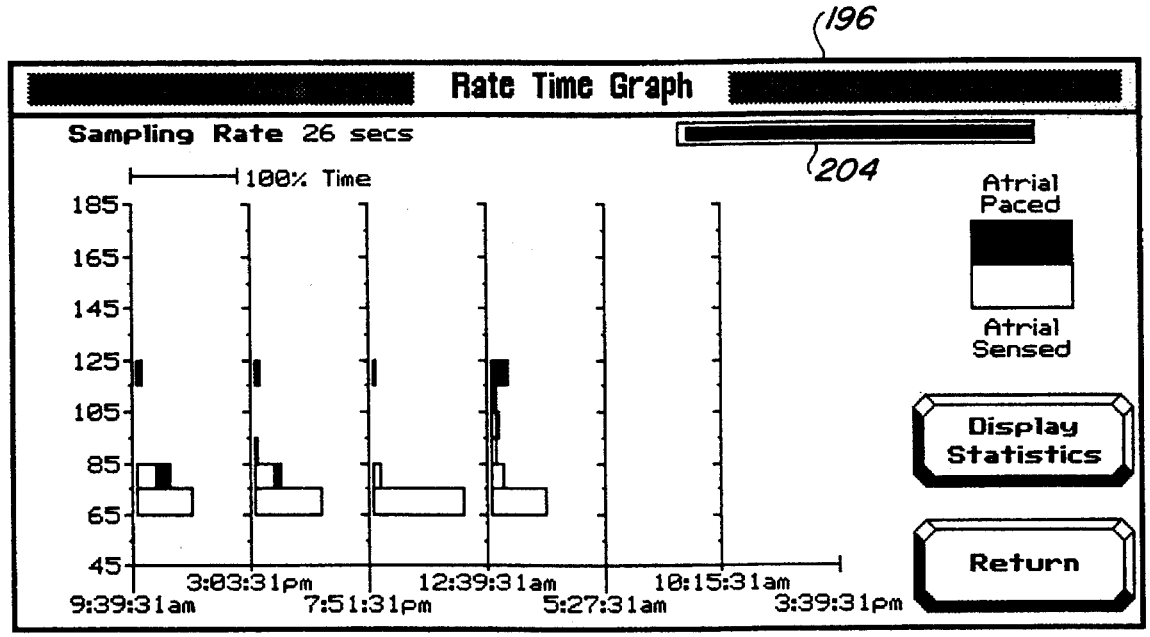
FIG. 16 shows a Rate Time Graph screen as displayed by the APS-II/MTM programmer showing typical histogram statistical summaries of the Event Record data as a function of rate and time, and percent of time paced or sensed.

The Select Statistics screen allows the user to select one of four types of graphical displays that display statistical information relative to the Event Record data in the current window displayed on the Event Record screen. These four types of display are: an Event Bar Graph (FIG. 13); a Rate Bar Graph (FIG. 14); a Rate Time Graph (FIG. 15); and an Event Time Graph (FIG. 16). All of these screens relating to the Event Record and related statistical information are described more fully below.

Referring next to FIG. 9, a typical Event Record screen 186 is shown. The screen 186 is displayed using the APS-II/MTM external programmer with a 30 hour time scale. The time scale is selected using the thumbwheel icon 202, located immediately below the Model and Serial No. information in the upper right hand corner of the screen. Thirty (30) hours is the maximum time scale that can be selected. Different time scales are selected by simply touching a lower or higher number. The amount of data included in the current window display is evident from a window content indicator 204. The window content indicator 204 includes a long, rectangular box 205 having a shaded bar 206 therein. The box symbolizes the entire Event Record. The shaded bar 206 inside of the box 205 symbolizes how much of the entire Event Record is currently displayed on the Event Record screen 186. For the example shown in FIG. 8, the bar 205 fills the box 206, indicating that the entire Event record is displayed in the screen 186.

Included in the upper left hand corner of the Event Record screen 186 is an indication of the sampling rate. For the example shown, the sampling rate is 26 seconds. Included across the bottom of the screen are five buttons: a "Read Event Record" button 208, a "Sampling Rate" button 210, a "Sensor Parameters" button 212, a left scroll button 214, and a right scroll button 216. A "Display Statistics" button 218 is positioned above the right scroll button 216. An icon "key" is presented between the time scale thumbwheel icon 202 and the Display Statistics button 218. Such key shows the symbols that are used on the Event Record screen to represent single pacing events. The key 220 shows, for example, that an "A" in reverse video (dark background, light letters) is the symbol for an AV event; while a normal "A" (light background, dark letters) is the symbol for an AR event. Likewise a "P" in reverse video is used to represent a PV event; while a normal "P" is used to represent a PR event. An "*" is the symbol for a PVE event, and an "o" is the symbol for OFF. If only single-chamber pacing is programmed or available, then a "S" in reverse video indicates a paced event; while a normal "S" indicates a sensed event. (The letter "S" is taken from the NBG code allowed for manufacturers to designate single-chamber pacing without knowing in advance whether the device will be used in the atrium or the ventricle.)

The Event Record is displayed in an essentially two dimensional graph that includes a rate scale 230 along the vertical axis, and a time scale 232 along the horizontal axis. One of the important features of the invention is that the Sample Event data that makes up the Event Record is time logged by the APS-II/MTM programmer. That is, the Event Sample itself only includes a type indicator and a rate indicator. However, because the Event Samples are recorded at a known rate, the Sample Rate, and because the data in the Event Record is always current, the APS-II/MTM processing circuits, which include a real time clock, can mark the time of the most recent Event Sample, and then work backwards in time, assigning each Event Sample an appropriate time of occurrence. (Alternately, a real time clock could be included in the pacemaker, and it could be used to make the time of events in the Event Record.) If the Sample Rate is 1.6 or 26 seconds, such time assignments are precisely accurate. If the Sample Rate is Every Event, then such time assignments are approximate based on the average pacing rate.

Once each Event Sample in the Event Record data is assigned a time of occurrence, the data is grouped by events into time slots determined by the total time to be displayed. At present, the width of the screen is divided into some 50 time slots. Thus, depending upon the time scale that is desired, one or more pacing events may fall into each time slot.

When more than one event falls into the same time slot, the multiple events are depicted as a vertical line 234 at each time slot. The top of the line is positioned relative to the rate axis or scale 230 to represent the maximum rate of all the events that are within that time slot. The bottom of the line is similarly positioned to represent the minimum rate of all the events that are within that time slot. A tick mark 236 represents the average rate of all the events that are in the time slot. Thus, by simply glancing at the Event Record containing the display of multiple events in the same time slots, such as is shown in FIG. 9, it is immediately apparent what the ranges of the paced events were, and what the average rates were, at a particular time.

Still referring to FIG. 9 in the preferred embodiment, a broad light line 222 may appear in the center of the Event Record screen 186. This broad light line 222 provides a reference marker for scrolling and otherwise examining the data. A bold line 224 is used to mark when a magnet is applied to the pacemaker. The mode of the pacer up to the point of the bold marker line 224, using the conventional three letter code, is indicated near the top of the marker line at 226. As indicated above, the presence of a magnet suspends the collection of the Event Record data. Given that time sequence is an essential feature of the Event Record, the bold or heavy marker 224 thus identifies when data collection is halted, even if only transiently. Thus, a patient may sense something abnormal, such as an intermittent palpitation. The patient may by instructed by the physician to place a magnet over the pacemaker when the palpitations are experienced. This results in a mark being placed in the Event Record at that time. The patient may then go to the physicians office where the Event Record data may be retrieved directly from the pacemaker and examined in order to determine the events that led up to the palpitations.

A dashed line 228 at the left of the Event Record data marks the left-hand edge of the available data.

Referring next to FIG. 10, a typical Event Record screen 188 is shown as displayed on the APS-II/MTM external programmer with a 1 minute time scale. In many respects, FIG. 10 is very similar to FIG. 9. However, note the window content indicator 204 shows a very small bar 206 inside of the box 205. Thus, that which is shown of the screen represents a window looking at just a tiny sliver of the overall Event Record. Moreover, the location of the bar 206 within the box 205 points out where in the Event Record data the current window is looking. By scrolling with the left scroll button 214, the bar 206 would move to the left within the box 205, and the data displayed on the Event Record screen would scroll backwards in time. By scrolling with the right scroll button 216, the bar 206 would move to the right within the box 205, and the data displayed on the Event Record screen would scroll forwards in time. However, for the example shown in FIG. 10, the data displayed is almost to the right edge of available data. Hence, it would not be possible to scroll very far to the right before reaching the right edge (most recent Event Sample data) of the Event Record.

As seen in FIG. 10, when the time scale is a low number, such as 1 minute, the Event Record is depicted as a series of literal events, represented by the icon symbols 232 and 233, representing AV and PV events, respectively. The horizontal lines 234 represent multiple samples of identical value. Increasing the time scale resolution to 15 seconds, using the thumbwheel icon selector 202, would display the entire window as letters representing discrete pacemaker events.

FIG. 11 illustrates a representation of the information included in a typical Event Record report as printed by the APS-II/MTM programmer for the data shown in FIG. 9. Note that the printout includes additional data not shown in the Event Record screen 186 due to the limited space available within the APS-II/MTM screen display. Such additional information includes an indication of the operating parameters of the pacemaker, such as its Mode, whether the Sensor is ON, OFF, or PASSIVE, the programmed rate, the maximum tracking rate, the maximum sensor rate, the programmed A-V Delay, and whether the rate-responsive A-V Delay is in an ENABLE or DISABLE state.

FIG. 12 shows the Select Statistics Format screen 190 that is displayed whenever the "Display Statistics" button is pressed on the Event Record screen. The Select Statistics screen is used as a launching point into one of the four types of graphical statistical displays. Five icon buttons are displayed on the Select Statistics screen. They are: an Event Bar Graph button 240, an Event Time Graph button 242, a Rate Bar Graph button 244, a Rate Time Graph button 246, and a Return button 248. The Select Statistics screen 190 is a popup screen that appears over the top of the current Event Record screen.

Figure 13:
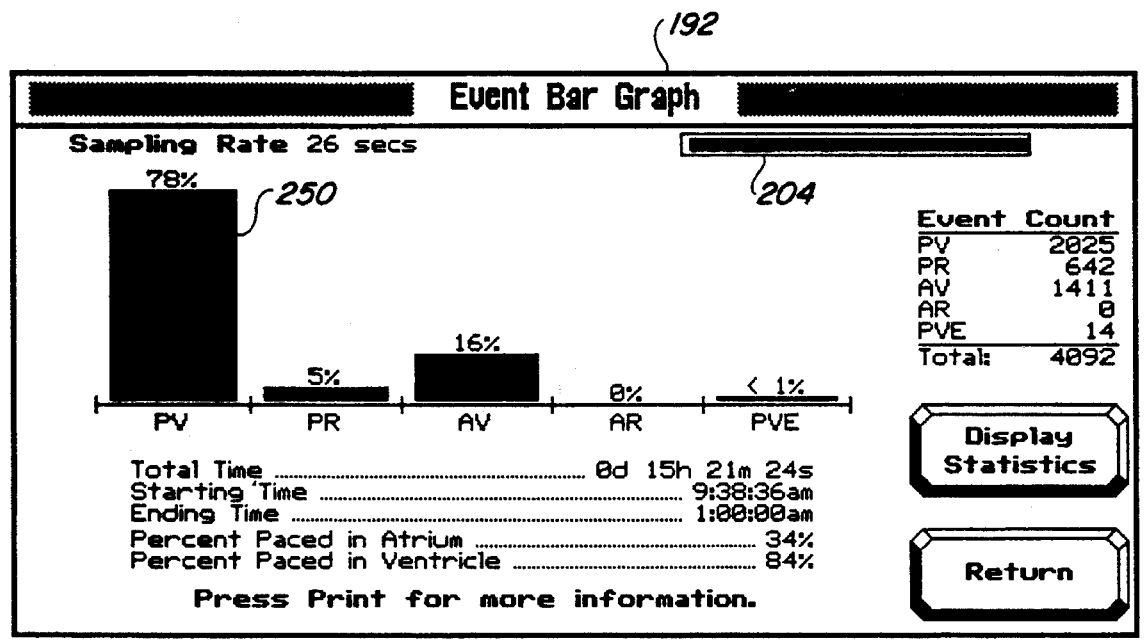
FIG. 13 shows an Event Bar Graph screen as displayed by the APS-II/MTM programmer showing typical histogram statistical summaries of the Event Record data as a function of event.

When the Event Bar Graph button 240 is pressed on the Select Statistic screen 190, an Event Bar Graph 192 is generated and displayed by the APS-II/MTM programmer. A representative Event Bar Graph 192 is shown in FIG. 13. The Event Bar Graph shows a histogram distribution of the event types displayed in the time window when the Select Statistics button was pressed. The window content indicator 204 is included as part of the graph. From the window content indicator shown in FIG. 13, it is quickly apparent that the displayed statistical histogram includes the entire Event Record. The histogram distribution is represented by a bar for each event type. The relative length or height of each bar in the Event Bar Graph represents the percentage of total time the pacemaker generated each event type. Above each histogram bar the percentage is presented in numeric form. Thus, by way of example, the bar 250, which shows the PV events, and is by far the highest bar of those shown, represents 78% of the event types. Moreover, a table of event counts is provided. Calculations are performed to compute the sum of counts for reach event type and the total event count. Additional calculations show the total time sampled, the percentage of counts paced in the atrium and ventricle, and total time at the Max Track Rate.

Figure 14:
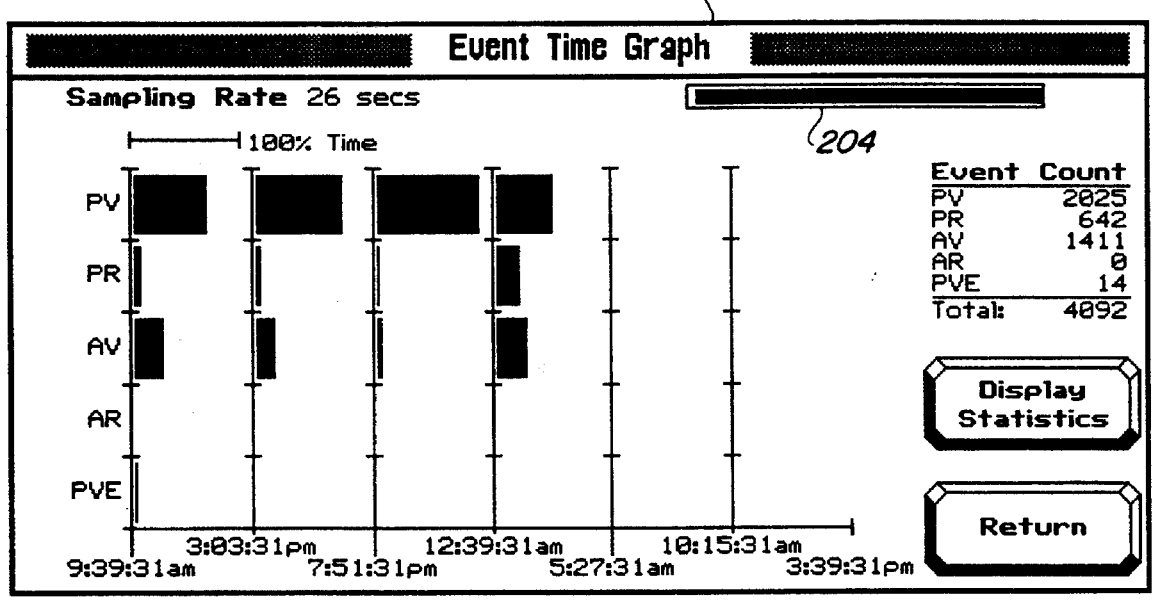
FIG. 14 shows an Event Time Graph screen as displayed by the APS-II/MTM programmer showing typical histogram statistical summaries of the Event Record data as a function of time and event.

When the Event Time Graph button 242 is pressed on the Select Statistics screen 190, an Event Time Graph 198 is generated and displayed by the APS-II/MTM programmer. A representative Event Time Graph 198 is shown in FIG. 14. The Event Time Graph shows multiple histogram distribution of event types in five separate time ranges within the selected time window. Each bar represents the percentage of time the pacemaker generated each event type during one fifth of the time window. Note that the window content indicator 204 is also shown with the graph.

When the Rate Bar Graph button 244 is pressed on the Select Statistics screen 190, a Rate Bar Graph 194 is generated and displayed by the APS-II/MTM programmer. A representative Rate Bar Graph 194 is shown in FIG. 15. The Rate Bar Graph shows a histogram distribution of event rates in the time window. Each bar represents the percentage of total time the pacemaker generated each event (atrial paced or atrial sensed) at a given rate. Calculations are performed to compute the total time sampled and the percentage of counts paced in the atrium and ventricle. Again, the window content indicator 204 is shown with the graph.

When the Rate Time Graph button 246 is pressed on the Select Statistics screen 190, a Rate Time Graph 196 is generated and displayed by the APS-II/MTM programmer. A representative Rate Time Graph 196 is shown in FIG. 16. The Rate Time Graph shows multiple histogram distribution of event rates in five separate time ranges within the selected time window. Each bar represents the percentage of time the pacemaker generated each event at a given rate during one fifth of the time window. Calculations are performed to compute the percentage of counts paced in the atrium and ventricle. The window content indicator 204 is included as part of the graph.

Referring next to FIG. 17, there is shown a representation of the information included in a typical Event Record report of the Event Bar Graph 192 as printed by the APS-II/MTM programmer. The report shown in FIG. 17 is based on data collected using a sampling time of 26 seconds (corresponding to a data collection period of around 30 hours), Note, the window content indicator 204 is included as part of the report. Note also that, like most printed reports generated by the APS-II/MTM, additional information is included in the printed report that is not included is the displayed screen.

FIG. 18 shows a typical Event Record report of the Event Time Graph 198 as printed by the APS-II/MTM programmer. Like FIG. 17, this report is based on data collected using a sampling time of 26 seconds, and includes the entire Event Record, as is evident from the window content indicator 204.

FIG. 19 similarly shows a typical Event Record report of the Rate Bar Graph 194 as printed by the APS-II/MTM programmer. The report shown is based on data collected using a sampling time of 26 seconds, and includes the entire Event Record.

FIG. 20 likewise shows a typical Event Record report of the Rate Time Graph 196 as printed by the APS-II/MTM programmer. This report is also based on data collected using a sampling time of 26 seconds, and the Event Samples in the entire Event Record.

It is noted that the reports shown in FIGS. 17–20 may be printed by pressing the print button 243 located on the APS-II/MTM programmer below the screen display (see FIG. 4).

It is further noted that, although the Sample Events are classified or typed in accordance with one of the seven event type designators described above in Table 2, the P@MTR-V and P@MTR-R events are not displayed in the Event Record. Rather, as displayed, a P@MTR-V event and a P@MTR-R event appear as PV and PR events, respectively.

There are numerous methods and techniques which may readily be used by those skilled in the art to create the displays and statistical information described above. The approach used in the APS-II/MTM programmer is to define a serious of routines, or programs, that control the processing circuits of the APS-II/MTM programmer. Advantageously, such programs may be stored in the detachable program cartridge 86. The APS-II/MTM is programmed to essentially remain in a wait state until some command is received. Upon receipt of a given command, the desired action is taken. Such action may involve, for example, retrieving Event Record data from the circular buffer memory 120 within the implantable pacemaker, processing the data to display the Event Record as a function of the time scale selected (FIGS. 9 and 10), or processing the data to create the displays shown in FIGS. 13–16. Other supporting routines define some specific action, such as scrolling left, that may be required once a primary action, such as displaying the Event Record screen, has taken place. A summary of the key primary and supporting routines used within the APS-II/MTM programmer in accordance with the present invention is presented in Table 4.

TABLE 4

| | | Event Record Routines Used In Creating The Event Record Display |
|---|---|---|
| 1. | Name: | event_record |
| | Called: | when Event Record button is pressed from Sensor Parameter Screen. |
| | Function: | Sets up the Event Record display. Draws an essentially blank display, showing the model/serial numbers, and the event record buttons (some of which are inactive until the event record is interrogated). |
| | Returns: | Nothing. |
| 2. | Name: | rderec_hit |
| | Called: | when Read Event Record key is pressed. |
| | Function: | Attempts to interrogate the event record. If successful, the event record screen is displayed by invoking the routine disp_erec (see item 10 below). |
| | Returns: | The event record data for inclusion in Event Record screen if interrogation is successful. |
| 3. | Name: | set_samp_hit |
| | Called: | when Sampling Rate button is pressed. |
| | Function: | Presents a pop-up to allow programming the event record sampling rate. The pop-up contains the sampling rate (SR) thumbwheel, the OK-Confirm button, and the Cancel button. |
| | Returns: | Nothing. |
| 4. | Name: | erec_conf_hit |
| | Called: | when the OK-Confirm button in the event record sampling rate pop-up is pressed. |
| | Function: | Attempts to program the selected sampling rate. |
| | Returns: | Nothing. |
| 5. | Name: | erec_lscroll_hit |
| | Called: | when left scroll arrow (←) is pressed. |
| | Function: | Scrolls the Event Record graph left, causing the events on the left side of the graph to be erased, and new events to appear on the right side. Right scrolling is ignored when the latest event reaches the center of the graph. |
| | Returns: | Nothing. |
| 6. | Name: | erec_rscroll_hit |
| | Called: | when right scroll arrow (→) is pressed. |
| | Function: | Scrolls the Event Record graph right, causing the events on the right side of the graph to be erased, and new events to appear on the left side. Left scrolling is ignored when the oldest event reaches the center of the graph. |
| | Returns: | Nothing. |
| 7. | Name: | erec_scale_hit |
| | Called: | when the event record time scale thumbwheel is pressed. |
| | Function: | Combines the previous time scale with the new time scale to adjust the time of the right side of the graph to maintain the same time at the center of the graph after changing time scales. |
| | Returns: | Nothing. |
| 8. | Name: | disp_erec_samprate |
| | Called: | as part of the event record screen display. |
| | Function: | displays the sampling rate for the event record currently displayed in the event record graph, not the currently programmed sampling rate. If the events on the display occurred at more than one sampling rate, then "various" is displayed. |
| | Returns: | Nothing. |
| 9. | Name: | draw_eventkey |
| | Called: | as required as part of the event record screen display. |
| | Function: | draws the legend ("key") that maps each single event icon to its event type. |
| | Returns: | Nothing. |
| 10. | Name: | disp_erec |
| | Called: | after the Read Event Record button is pressed if the interrogation is successful. |
| | Function: | Activates the scroll and stat buttons, redraws the scale thumbwheel, and draws the event record display. |
| | Returns: | Nothing. |
| 11. | Name: | correct_left_event |

TABLE 4-continued

Event Record Routines Used In
Creating The Event Record Display

|   |   |   |
|---|---|---|
|   | Called: | from the Event Record scroll button functions after events have been drawn or erased from the graph. |
|   | Function: | Makes sure left events appear before right events; if not, adjusts left events. Checks if the left and right events have become reversed: that is, the record time of the left event must be less than that of the right event. Reversal could otherwise occur when the left and right events are equal before scrolling occurs. |
|   | Returns: | Nothing. |
| 12. | Name: | correct_right_event |
|   | Called: | from the Event Record scroll button functions after events have been drawn or erased from the graph. |
|   | Function: | Makes sure right events appear after left events; if not, adjusts right events. Checks if the left and right events have become reversed: that is, the record time of the left event must be less than that of the right event. Reversal could otherwise occur when the left and right events are equal before scrolling occurs. |
|   | Returns: | Nothing. |
| 13. | Name: | at_left_limit |
|   | Called: | from the Event Record scrolling function erec_lscroll_hit (item No. 5 above) and the scale-change function erec_scale_hit (item No. 7 above). |
|   | Function: | Determines if the right-most event in the Event Record has been scrolled or scaled to the left-most permissible point in the graph window. |
|   | Returns: | YES, if the left-most limit has been reached or exceeded; or NO, if the left-most limit has not been reached. |
| 14. | Name: | at_right_limit |
|   | Called: | from the Event Record scrolling function erec_rscroll_hit (item No. 6 above) and the scale-change function erec_scale_hit (item No. 7 above). |
|   | Function: | Determines if the left-most event in the Event Record has been scrolled or scaled to the right-most permissible point in the graph window. |
|   | Returns: | YES, if the right-most limit has been reached or exceeded; or NO, if the right-most limit has not been reached. |

Advantageously, using the Event Record as described above, a physician is thus able to assess the performance of the pacing system over time, including time when the patient is not in the physician's office. The Event Record thus serves essentially the same function as a Holter Monitor, but it does so without the inconvenience, bother, and expense of a Holter Monitor. The Event Record advantageously places various pacing states into a time relationship with one another, thereby allowing the physician to have a better appreciation as to how the system is functioning, thus facilitating a correlation between any symptoms or activities with the performance of the pacing system. Although the Event Record can only store a relatively small amount of data, e.g, 4096 Event Samples in the current embodiment, a significant amount of information can still be learned. For example, by using a sampling rate of 1.6 seconds, roughly 2 hours of pacing event data is collected. By using a sampling rate of 26 seconds, almost 30 hours of data is collected. The paper by Levine, D.A., entitled "Utility and Clinical Benefits of Extensive Event Counter Telemetry in the Follow-Up and Management of the Rate-Modulated Pacemaker Patient," published by Siemens Pacesetter, Inc., 15900 Valley View Court, Sylmar, Calif. 91392 (February 1992), incorporated herein by reference, is a manuscript that describes several examples of how the present invention and other related inventions may be used to assist a physician in optimally programming a pacemaker for a particular patient and in providing better understanding of the interaction of the pacemaker and the patient over a variable period of time.

There are also several variations of the invention that may be made. For example, additional information may be added to the Event Record samples. In addition to the event type and rate information presently included in the samples, additional bits could be added to the Event Sample data word to include:

(1) The Sensor-Indicated Rate.

(2) Raw sensor information (i.e, the sensor input signal before processing).

(3) Pacemaker state information (such as activation of a PMT algorithm, or a PVC response, stages of a Tachycardia Detection algorithm, or stages of an Automatic Capture Test.

(4) P-wave and/or R-wave amplitudes.

(5) Atrial and/or Ventricular Lead Impedance.

(6) Data concerning individual sensor performance where more than one sensor is utilized.

Also, a small, hand-held, read-only programmer may be provided to the patient so that the patient would be able to immediately capture the Event Record in the event of experiencing palpitations or other problems.

Further, in some embodiments, the pacemaker may have a portion of its memory designated as a capture buffer memory. Upon receipt of a trigger signal, the contents of the Event Record are transferred to the capture buffer memory where they are saved until retrieved by a physician through using an appropriately programmed APS-II/MTM or similar device. The trigger signal would be generated by the patient, e.g., by applying a magnet to the pacemaker. Alternatively, the trigger signal could be generated automatically, based on a prescribed detection criteria.

While the invention herein disclosed has been described by means of specific embodiments and applications thereof, numerous modifications and variations could be made thereto by those skilled in the art without departing from the scope of the invention set forth in the claims.

What is claimed is:

1. A system for reporting a sequential series of pacing events for use with an implantable pacemaker, said implantable pacemaker having means for storing pacing event data and means for telemetrically transmitting said pacing event data, said system comprising:

means for telemetrically receiving said pacing event data;

means for displaying a rate axis;

means for displaying a time axis orthogonal to the rate axis;

means for displaying a plurality of symbols arranged in a timed sequence relative to the time axis, said symbols representing pacing events, as recorded within said pacing event data, that have occurred in the sequence displayed, said symbols being positioned relative to the rate axis to indicate the rate at which the pacing events occurred; and means for displaying a time scale indication that provides a graphical depiction of the time scale associated with the displayed timed sequence of symbols, and an indication of how much of the total time represented by said pacing event data is currently being displayed.

2. A method of reporting a sequential series of pacing events associated with the operation of an implantable pacemaker, said method comprising the steps of:

(a) displaying a horizontal time axis and a vertical rate axis;

(b) dividing the horizontal time axis into a plurality of time slots;

(c) electronically gathering event and rate data in a sequence that identifies specific pacing events, the rate of those specific pacing events, and the order in which such specific pacing events occurred;

(d) grouping said event and rate data in a plurality of event/rate data groups, each group corresponding to a respective one of said time slots;

(e) determining the maximum and minimum rates of the specific pacing events of each of said plurality of event/rate data groups; and (f) displaying a plurality of vertical first features, each of said vertical first features being displayed above a respective one of said time slots, each vertical first feature representing a respective one of said plurality of event/rate data groups, each vertical first feature being positioned relative to the vertical axis such that the top of the vertical first feature corresponds to the maximum rate of the respective one of said plurality of event/rate data groups, and the bottom of the vertical first feature corresponds to the minimum rate of the respective one of said plurality of event/rate data groups.

3. The method, as set forth in claim 2, wherein step (e) further includes:

determining the average rate of the specific pacing events of each of said plurality of event/rate data groups; and step (f) further includes:

displaying a second feature on each of said vertical first features at a location relative to said rate axis, wherein said second feature indicates the average rate of the respective one of said plurality of event/rate data groups.

4. The method, as set forth in claim 3, wherein step (a) includes selecting a time scale and displaying said horizontal time axis using said selected time scale.

5. The method, as set forth in claim 4, further including:

computing statistical information associated with said plurality of said event/rate data groups, and selectively displaying said statistical information.

6. An event record display apparatus for displaying a sequential series of pacing events associated with the operation of an implantable pacemaker, said event record display apparatus comprising:

means for displaying a time axis;

means for displaying a plurality of time slots on said time axis;

means for displaying a rate axis orthogonal to said time axis;

means for gathering event data and rate data in sequence, said event data and rate data identifying specific pacing events and the order in which such specific pacing events occurred;

means for grouping said event and rate data into a plurality of event/rate data groups;

means for processing said plurality of event and rate date groups to determine a plurality of histograms representing the specific pacing events of said event and rate data corresponding to the respective ones of said plurality of event/rate data groups; and means for graphically displaying said plurality of histograms each of said histograms being displayed above a respective one of said plurality of time slots.

7. An event record display apparatus, as set forth in claim 6, wherein said means for graphically depicting further comprises:

means for determining the average rate of the specific pacing events represented by said plurality of histograms;

means for displaying a plurality of features, each of said features being displayed near a respective one of said plurality of histograms, each of said features being placed at a location relative to said rate axis so as to indicate the average rate of the specific pacing events represented by said respective one of said plurality of histograms.

8. An event record display apparatus, as set forth in claim 6, further comprising:

means for selecting a time scale and displaying said time axis using said selected time scale.

9. An event record display apparatus, as set forth in claim 6, wherein said means for grouping comprises means for selecting a portion of said event and rate data to be included in said plurality of event/rate data groups.

10. An event record display apparatus, as set forth in claim 6, further comprising:

means for computing statistical information associated with the pacing events represented by said plurality of histograms, and selectively displaying said statistical information.

11. An event record display apparatus, as set forth in claim 6, further comprising:

means for displaying a time scale indication that provides a graphical depiction of the time scale associated with said time axis; and means for displaying an indication of how much of the total time represented by said event data and rate data is represented by said histograms.

12. An event record display apparatus, as set forth in claim 6, wherein the implantable pacemaker detects the occurrence and the rate of a plurality of specified pacing events and sequentially records the occurrence and rate of each event in the order in which it occurs in an event record, the implantable pacemaker including means for telemetrically transmitting said event record, wherein said gathering means further comprises:

means for telemetrically receiving said event record from said pacemaker; and means for processing said event record for determining event data and rate data in a sequence identifying specific pacing events and the order in which such specific pacing events occurred.

13. An event record display apparatus for displaying a sequential series of pacing events associated with the operation of an implantable pacemaker, wherein said pacemaker has a plurality of buffer memories for storing pacing events and for storing the rate of said pacing events, said event record display apparatus comprising:

means for designating a specific one of the buffer memories within said pacemaker;

means for displaying a time axis;

means for displaying a plurality of time slots on said time axis;

means for displaying a rate axis orthogonal to said time axis;

means for gathering event data and rate data in a sequence from said designated buffer memory that identifies specific pacing events and the order in which such specific pacing events occurred; and means for graphically depicting a plurality of histograms representing the specific pacing events identified in said event data and rate data that occurred during a time period corresponding to a respective one of said plurality of time slots.

14. A system for reporting a sequential series of events for use with an implantable cardiac device, said implantable cardiac device having means for storing event data and means for telemetrically transmitting said event data, said system comprising:

means for telemetrically receiving said event data;

means for displaying a rate axis;

means for displaying a time axis orthogonal to the rate axis; and means for displaying a plurality of symbols arranged in a timed sequence relative to said time axis, said symbols representing events, as recorded within said event data, that have occurred in the sequence displayed, said symbols being positioned relative to the rate axis to indicate the rate at which the corresponding events occurred.

15. A system, as set forth in claim 14, further comprising:

means for selecting which events are to be represented by said display plurality of symbols.

16. A system, as set forth in claim 15, further comprising:

means for providing an indication of how much of the total time represented by said sequential series of events is currently selected.

17. A method of reporting a sequential series of pacing events associated with the operation of an implantable pacemaker, wherein the pacemaker detects the occurrence and rate of a plurality of specified pacing events and sequentially records the occurrence and rate of each event in the order in which it occurs in an event record, said method comprising the steps of:

(a) displaying a time axis divided into a plurality of time slots and a rate axis orthogonal to the time axis;

(b) retrieving from said pacemaker said event record;

(c) processing said event record to determine event data and rate data and identify specific pacing events and the order in which such specific pacing events occurred;

(d) grouping said event data and rate data in a plurality of event/rate data groups, each group corresponding to a respective one of said plurality of time slots;

(e) determining the maximum and minimum rates of the specific pacing events of each of said plurality of event/rate data groups; and (f) displaying a plurality of first features having a first end and a second end, each of said first features being displayed above a respective one of said plurality of time slots, each of said first features representing a respective one of said plurality of event/rate data groups corresponding to said respective one of said plurality of time slots, each said first feature being positioned relative to said rate axis such that said first end of each said first feature corresponds to the maximum rate of the pacing events represented by said first feature, and said second end of each said first feature corresponds to the minimum rate of the pacing events represented by each said first feature.

18. The method, as set forth in claim 17, additionally comprising:

(g) determining the average rate of the specific pacing events of each of said plurality of event/rate data groups: and (h) displaying a second feature on each of said first features at a location relative to said rate axis that indicates the average rate of the respective one of said plurality of event/rate data groups.

19. The method, as set forth in claim 18, wherein step (a) comprises:

selecting a time scale and displaying said time axis using said selected time scale.

20. The method, as set forth in claim 17, wherein step (d) comprises:

selecting a portion of said event data and rate data to be represented by said plurality of event/rate data groups.

21. The method, as set forth in claim 17, further comprising:

(g) computing statistical information associated with said plurality of said event/rate data groups, and selectively displaying said statistical information.

22. A system for reporting a sequential series of cardiac events for use with an implantable cardiac device, said implantable cardiac device including means for storing cardiac event data and means for telemetrically transmitting said cardiac event data, said system comprising:

means for telemetrically receiving said cardiac event data;

means for displaying a rate axis;

means for displaying a time axis orthogonal to the rate axis; and means for displaying a plurality of symbols arranged in a timed sequence relative to said time axis, said symbols representing cardiac events, as recorded within said cardiac event data, that have occurred in the sequence displayed, said symbols being positioned relative to the rate axis to indicate the rate at which the corresponding cardiac events occurred.

23. A system, as set forth in claim 22, further comprising:

means for selecting which cardiac events are to be displayed.

24. A system, as set forth in claim 23, further comprising:

means for providing an indication of how much of the total time represented by said sequential series of cardiac events is currently selected.

25. A system, as set forth in claim 23, wherein said implantable cardiac device further includes means for sensing R-waves and said cardiac events comprise sensed R-waves, said plurality of symbols comprising:

symbols indicating sensed R-waves.

26. A system, as set forth in claim 25, wherein said implantable cardiac device further includes means for generating V-pulses and said cardiac events further comprise generated V-pulses, said plurality of symbols further comprising:

symbols indicating generated V-pulses.

27. A System, as set forth in claim 26, wherein said implantable cardiac device further includes means for sensing P-waves and said cardiac events comprise sensed P-waves, said plurality of symbols further comprising:

symbols indicating sensed P-waves.

28. A system, as set forth in claim 27, wherein said implantable cardiac device further includes means for generating A-pulses and said cardiac events further comprise generated A-pulses, said plurality of symbols further comprising:

symbols indicating generated A-pulses.

29. A system, as set forth in claim 28, wherein said cardiac events further comprise "PR" events indicating a P-wave followed by an R-wave, "PV" events indicating a P-wave followed by a V-pulse, "AR" events indicating an A-pulse followed by an R-wave, and "AV" events indicating an A-pulse followed by a V-wave, said plurality of symbols further comprising:

symbols indicating "PR" events, "PV" events, "AR" events, and "AV" events.

30. A system, as set forth in claim 29, wherein said cardiac events further comprise "PVE" events indicating an R-wave followed by another R-wave or a V-pulse followed by an R-wave said plurality of symbols further comprising:

symbols indicating "PVE" events.

31. A system, as set forth in claim 29, wherein said implantable cardiac device further includes means for defining a maximum tracking rate (MTR) interval that begins upon the occurrence of a prescribed cardiac event and continues for a prescribed time thereafter, and said cardiac events further comprise P-waves and R-waves detected during an MTR interval, said plurality of symbols further comprising:

symbols indicating P-waves detected during an MTR interval followed by a V-pulse and P-waves detected during an MTR interval followed by an R-wave.

32. A system, as set forth in claim 23, wherein said implantable cardiac device includes means for sensing P-waves and said cardiac events comprise sensed P-waves, said plurality of symbols comprising:

symbols indicating sensed P-waves.

33. A system, as set forth in claim 32, wherein said implantable cardiac device further includes means for generating A-pulses and said cardiac events further comprise generated A-pulses, said plurality of symbols further comprising:

symbols indicating generated A-pulses.

34. A system, as set forth in claim 33, wherein said implantable cardiac device includes means for sensing cardiac events and said cardiac events comprise sensed cardiac events, said plurality of symbols comprising:

symbols indicating sensed events.

35. A system, as set forth in claim 34, wherein said implantable cardiac device further includes means for generating paced events and said cardiac events further comprise paced events said plurality of symbols further comprising:

symbols indicating paced events.

* * * * *